US008466105B2

(12) United States Patent
Bix

(10) Patent No.: US 8,466,105 B2
(45) Date of Patent: Jun. 18, 2013

(54) TREATMENT OF STROKE USING DOMAIN V OF PERLECAN

(75) Inventor: Gregory J. Bix, College Station, TX (US)

(73) Assignee: The Texas A&M University System, College Station, TX (US)

( * ) Notice: Subject to any disclaimer, the term of this patent is extended or adjusted under 35 U.S.C. 154(b) by 464 days.

(21) Appl. No.: 12/655,503

(22) Filed: Dec. 31, 2009

(65) Prior Publication Data
US 2010/0168025 A1    Jul. 1, 2010

Related U.S. Application Data

(60) Provisional application No. 61/204,064, filed on Dec. 31, 2008.

(51) Int. Cl.
*C07K 14/515*    (2006.01)
*A61P 25/00*    (2006.01)

(52) U.S. Cl.
USPC ............. 514/13.3; 514/9.6; 514/54; 530/380; 530/350

(58) Field of Classification Search
None
See application file for complete search history.

(56) References Cited

U.S. PATENT DOCUMENTS
6,821,947 B2 * 11/2004 Iozzo ........................... 514/13.3

FOREIGN PATENT DOCUMENTS
WO    WO 03/048333    6/2003

OTHER PUBLICATIONS

Lee et al., The Journal of Clincial Investigation, 2011; 121: 3005-3023.*
Tokuriki and Tawflik, Current Opinion in Structural Biology 2009, 19: 596-604.*
Kallunki and Tryggvason, Journal of Cell Biology, 1992; 116: 559-571.*
Murdoch et al., JBC, 1992; 267: 8544-8557.*
Aronowski, J. et al. "Neurofilament Proteolysis After Focal Ischemia; When Do Cells Die After Experimental Stroke?" *Journal of Cerebral Blood Flow & Metabolism*, 1999, pp. 652-660, vol. 19.
Asou, H. et al. "Cell Adhesion molecule L1 guides cell migration in primary reaggregation cultures of mouse cerebellar cells" *Neuroscience Letters*, 1992, pp. 221-224, vol. 144.
Auerbach, R. et al. "Angiogenesis Assays: A Critical Overview" *Clinical Chemistry*, 2003, pp. 32-40, vol. 49, No. 1.
Bix, G. J. et al. "Platelet-Activating Factor Receptor Stimulation Disrupts Neuronal Migration in Vitro" *The Journal of Neuroscience*, Jan. 1, 1998, pp. 307-318, vol. 18, No. 1.
Bix, G. et al. "Matrix revolutions: 'tails' of basement-membrane components with angiostatic functions" *Trends in Cell Biology*, Jan. 2005, pp. 52-60, vol. 15, No. 1.
Bix, G. et al. "Endorepellin, the C-terminal angiostatic module of perlecan, enhances collagen-platelet response via the α2β1-intergrin receptor" *Blood*, May 1, 2007, pp. 3745-3748, vol. 109, No. 9.
Bix, G. et al. "Endorepellin In Vivo: Targeting the Tumor Vasculature and Retarding Cancer Growth and Metabolism" *Journal of the National Cancer Institute*, Nov. 15, 2006, pp. 1634-1646, vol. 98, No. 22.
Bix, G. et al. "Endorepellin causes endothelial cell disassembly of actin cytoskeleton and focal adhesions through α2β1 intergrin" *The Journal of Cell Biology*, Jul. 5, 2004, pp. 97-109, vol. 166, No. 1.
Brittingham, R. et al. "Single Amino Acid Substitutions in Procollagen VII Affect Early Stages of Assembly of Anchoring Fibrils" *The Journal of Biological Chemistry*, Jan. 7, 2005, pp. 191-198, vol. 280, No. 1.
Clarke, D. et al. "Endorepellin and Endostatin Affect the Neurovascular Unit in Vitro" *J. Neurochem.*, 2008, p. 1, vol. 104, Suppl. 1.
Hirotsune, S. et al. "Graded reduction of *Pafah1b1* (*Lis1*) activity results in neuronal migrating defects and early embryonic lethality" *Nature Genetics*, Aug. 1998, pp. 333-339, vol. 19.
Milner, R. et al. "Responses of Endothelial Cell and Astrocyte Matrix-Integrin Receptors to Ischemia Mimic Those Observed in the Neurovascular Unit" *Stroke*, 2008, pp. 191-197, vol. 39.
Mongiat, M. "Endorepellin, a Novel Inhibitor of Angiogenesis Derived from the C Terminus of Perlecan" *The Journal of Biological Chemistry*, Feb. 7, 2003, pp. 4238-4249, vol. 278, No. 6, XP-002547225.
Mundel, T. M. "Type IV collagen-derived angiogenesis inhibitors" *Microvascular Research*, 2007, pp. 85-89, vol. 74.
Myszka, D. G. et al. "CLAMP: a biosensor kinetic data analysis program" *TIBS*, Apr. 1998, pp. 1-2, vol. 23.
Ohab, J. J. et al. "A Neurovascular Niche for Neurogenesis after Stroke" *The Journal of Neuroscience*, Dec. 13, 2006, pp. 13007-13016, vol. 26, No. 50.
Ohwaki, K. et al. "Blood Pressure Management in Acute Intracerebral Hemorrhage Relationship between Elevated Blood Pressure and Hematoma Enlargment" *Stroke*, 2004, pp. 1364-1367, vol. 35.
O'Reilly, M. S. et al. "Endostatin: An Endogenous Inhibitor of Angiogenesis and Tumor Growth" *Cell*, Jan. 24, 1997, pp. 277-285, vol. 88.
O'Regan, C. et al. "Statin Therapy in Stroke Prevention: A Meta-analysis Involving 121,000 Patients" *The American Journal of Medicine*, 2008, pp. 24-33, vol. 121.
Hankey, G. J. "Statins after transient ischaemic attack and ischaemic stroke" *Neurology*, Oct. 2006, pp. 810-812, vol. 5.
Sapatino, B. V. et al. "Cloned Mouse Cerebrovascular Endothelial Cells That Maintain Their Differentiation Markers for Factor VIII, Low Density Lipoprotein, and Angiotensin-Converting Enzyme" *In Vitro Cellular & Developmental Biology*, Dec. 1993, pp. 923-928, vol. 29A, No. 12.
Schallert, T. et al. "Use-Dependent Structural Events in Recovery of Function" Brain Plasticity, *Advances in Neurology*, 1997, pp. 229-238, vol. 73.

* cited by examiner

*Primary Examiner* — Bridget E Bunner
*Assistant Examiner* — Christina Borgeest
(74) *Attorney, Agent, or Firm* — Saliwanchik, Lloyd & Eisenschenk

(57) ABSTRACT

The present invention is drawn to methods of stimulating or enhancing angiogenesis in a patient comprising, administering to said patient a therapeutically effective amount of an endorepellin protein, wherein said endorepellin protein has an amino acid sequence of domain V of perlecan or fragments or derivatives, analogs thereof; and stimulating or enhancing generation of blood vessels. The present invention is drawn to compositions for enhancing angiogenesis.

7 Claims, 17 Drawing Sheets
(2 of 17 Drawing Sheet(s) Filed in Color)

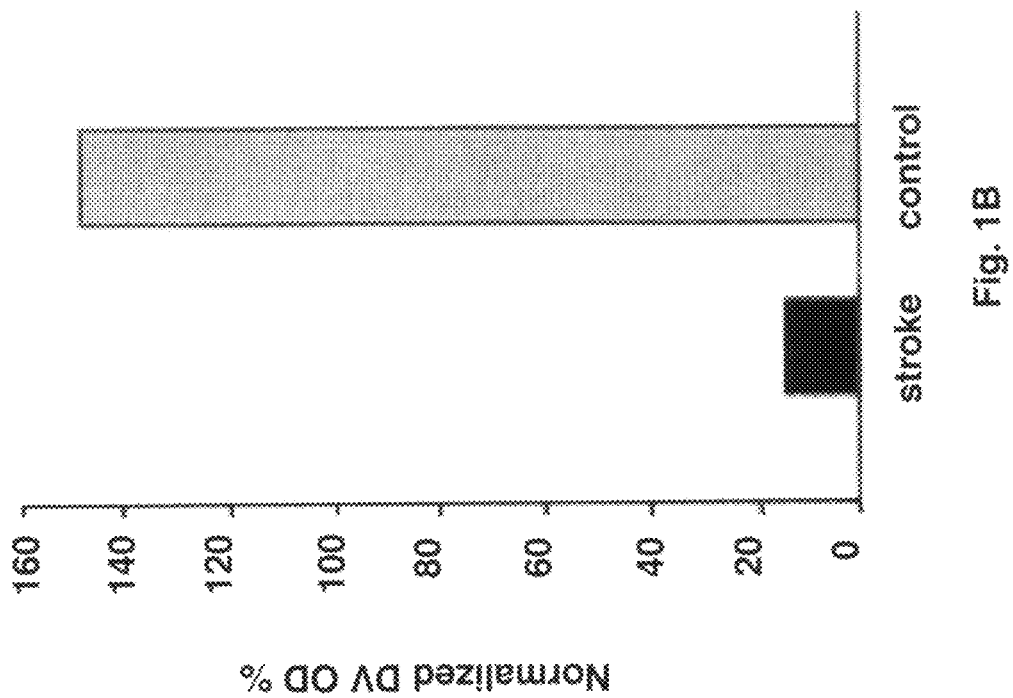
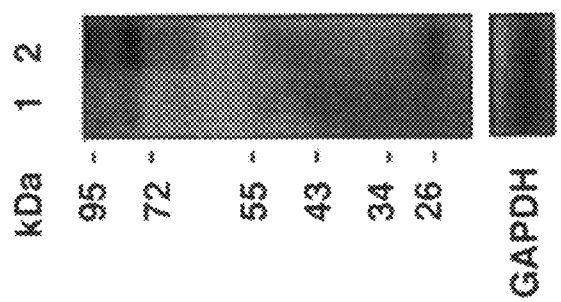

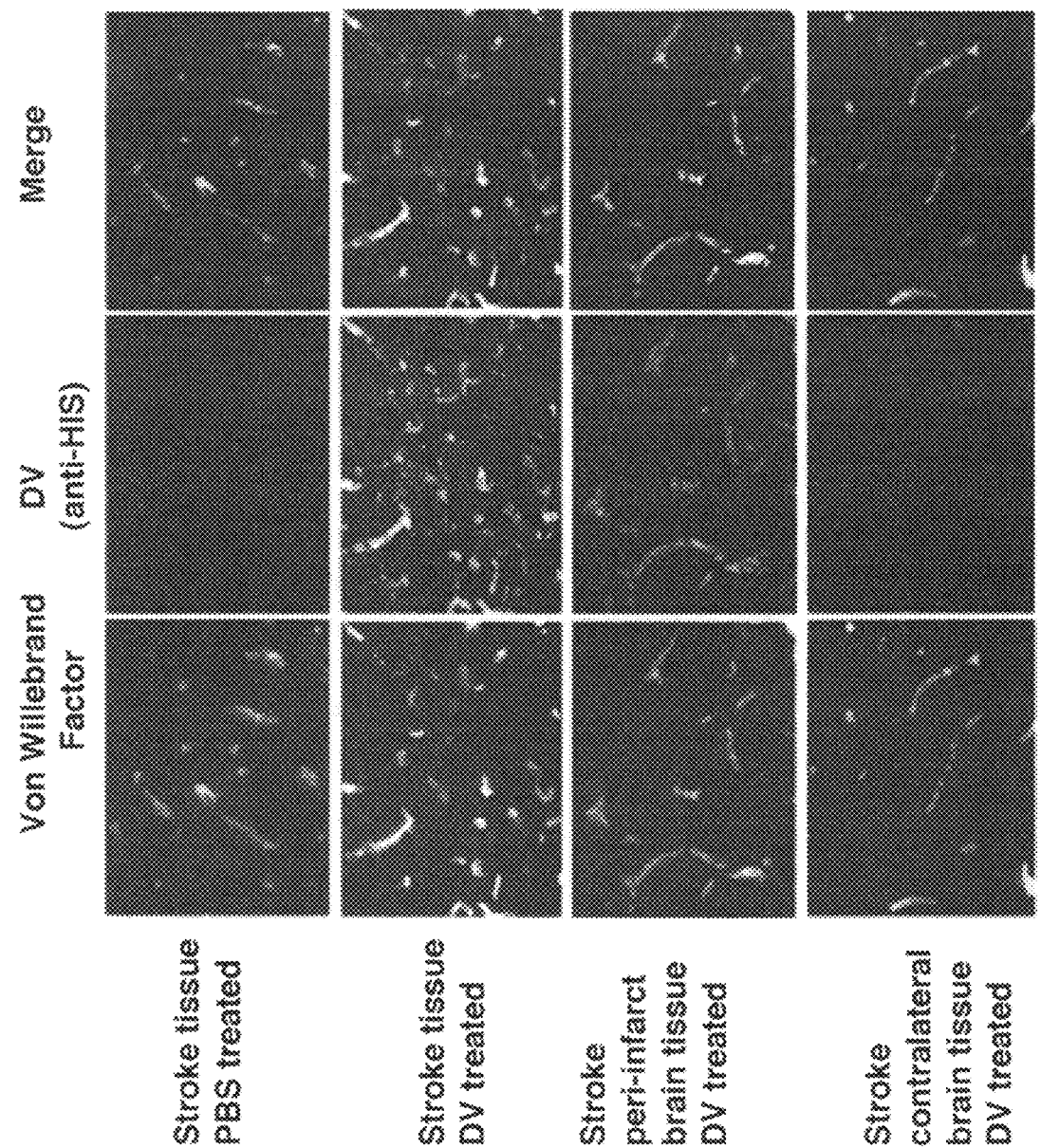

```
SEQUENCE LISTING

<160> NUMBER OF SEQ ID NOS: 3

<210> SEQ ID NO 1
<211> LENGTH: 5
<212> TYPE: PRT
<213> ORGANISM: artificial sequence
<220> FEATURE:
<223> OTHER INFORMATION: integrin RGD binding motif

<400> SEQUENCE: 1

Gly Arg Gly Asp Ser
1               5

<210> SEQ ID NO 2
<211> LENGTH: 5
<212> TYPE: PRT
<213> ORGANISM: artificial sequence
<220> FEATURE:
<223> OTHER INFORMATION: control peptide for integrin binding motif

<400> SEQUENCE: 2

Ser Asp Gly Arg Gly
1               5

<210> SEQ ID NO 3
<211> LENGTH: 9
<212> TYPE: PRT
<213> ORGANISM: artificial sequence
<220> FEATURE:
<223> OTHER INFORMATION: alpha5beta1 specific binding peptide

<400> SEQUENCE: 3

Cys Arg Arg Glu Thr Ala Trp Ala Cys
1               5
```

TREATMENT OF STROKE USING DOMAIN V OF PERLECAN

CROSS-REFERENCE TO RELATED APPLICATION

This nonprovisional application claims benefit of priority under 35 U.S.C. §119(e) of provisional U.S. Ser. No. 61/204,064, filed Dec. 31, 2008, now abandoned, the entirety of which is hereby incorporated by reference.

BACKGROUND OF THE INVENTION

1. Field of the Invention

The present invention relates generally to the field of stroke and angiogenesis. More specifically, the present invention relates to stroke-generated angiogenesis enhancers and uses thereof.

2. Description of the Related Art

Brain recovery from stroke is a complex system involving the restoration of blood supply (angiogenesis) and neurons (neurogenesis) to the affected area. For angiogenesis, endothelial cell proliferation can occur as early as 12 to 24 hours. These newly generated cells then migrate towards ischemic brain regions in response to a number of endothelial cell mitogens such as vascular endothelial cell growth factor (VEGF) and platelet derived growth factor (PDGF) and form new blood vessels in peri-infarct cortex after 3-7 days. Angiogenesis then continues for at least 21 days. Importantly, niaspan, a drug that increases post-stroke angiogenesis in rodents, improves functional stroke recovery, suggesting that enhancing post-stroke brain angiogenesis could result in improved stroke outcomes. Furthermore, brain angiogenesis is different from non-brain angiogenesis due to unique properties of the brain vasculature including formation of the blood-brain barrier, embedment in a neuronal-glial milieu, different matrix receptor expression, and relative refractoriness to angiogenesis after development.

Ohab et al. (1) have demonstrated in rodents that after stroke migrating immature neurons (neuroblasts) associate with remodeling blood vessels in a "neurovascular niche" that causally links reparative angiogenesis and neurogenesis. The newly produced vasculature promotes neurogenesis by production of various growth factors and appears to serve as a scaffold for newly born neurons that allows them to migrate towards infarcted tissue. In addition to maturing neurons and endothelial cells, the neurovascular niche contains extracellular matrix (ECM) that is secreted and actively remodeled during angiogenesis to allow cellular migration and blood vessel morphogenesis. One such extracellular matrix component, perlecan, is essential to the neurovascular niche. Its absence in mice results in severely impaired neurogenesis due to the loss of neurogenic factor capturing that perlecan provides to support neurogenesis.

Matrix remodeling during and after stroke is an important part of brain repair after injury and repair that further points to the importance of perlecan. In stroke, dying and infiltrating inflammatory cells release matrix metalloproteinases (MMPs) which disturb the blood brain barrier and proteolytically process the extracellular matrix. Although the initial processing and degradation of extracellular matrix is largely thought of as a negative consequence of stroke, one consequence of matrix proteolysis is the generation of bioactive matrix fragments. Indeed, many matrix components are known to harbor bioactive matrix fragments in their C-terminal regions that can inhibit angiogenesis outside of the central nervous system (2-3). Perlecan has the distinction of being the most sensitive and rapidly processed matrix component after stroke. Perlecan proteolysis occurs within 2 hours of the occlusion of the middle cerebral artery in nonhuman primates and persists for at least 7 days.

Perlecan is composed of five domains, each with sequence homology to other proteins. The C-terminal fragment of perlecan known as domain V (DV or endorepellin) consists of three laminin globular (LG) domains, each separated by two epidermal growth factor (EG)-like domains. Domain V and its LG3 fragment are normally found in the human urinary, blood and cerebrospinal fluid proteomes. Domain V, by binding to the $\alpha 2$ subunit of the $\alpha 2\beta 1$ integrin, inhibits several angiogenic functions of nonbrain endothelial cells including migration and capillary morphogenesis. Domain V interaction with $\alpha 2\beta 1$ appears to be different than that of pro-angiogenic collagen with $\alpha 2\beta 1$ resulting in opposing outcomes. Domain V has been characterized as anti-angiogenic in several endothelial cell types of nonbrain origin (4-5).

Despite this, the prior art is deficient in angiogenesis enhancers. The current invention fulfils this long standing need in the art.

SUMMARY OF THE INVENTION

The present invention shows that Domain V enhances brain angiogenesis and the interaction between endothelial cells and neurons in the neurovascular niche. Domain V interacts with, affects the cellular distribution of, and exerts its pro-angiogenic effect via the $\alpha 5\beta 1$ integrin. These observations are consistent with the lack of brain endothelial cell expression of the Domain V anti-angiogenic $\alpha 2\beta 1$ integrin, and with the concept that brain angiogenesis could be differently regulated than angiogenesis outside of the brain. Therefore, the present invention shows that Domain V, generated after stroke by increased and sustained proteolysis of perlecan, stimulates post-stroke angiogenesis, fosters the formation of the neurovascular niche necessary for post-stroke neurogenesis and directed neuroblast migration, and thereby is a component of the brain's self-repair mechanism that can be therapeutically exploited to improve stroke recovery.

In one embodiment of the present invention, there is provided a method of stimulating or enhancing angiogenesis in a patient comprising, administering to said patient a therapeutically effective amount of an endorepellin protein, wherein said endorepellin protein has an amino acid sequence of domain V of perlecan or fragments or derivatives, analogs thereof; and stimulating or enhancing generation of blood vessels.

In another related embodiment of the present invention, there is provided a method of stimulating or enhancing angiogenesis in a patient comprising, administering to said patient a therapeutically effective amount of an endostatin protein, or fragments or derivatives, analogs thereof; and stimulating or enhancing generation of blood vessels.

In another embodiment of the present invention, there is provided a pharmaceutical composition, comprising a domain V of perlecan or fragments or derivatives, analogs thereof, a statin and a pharmaceutically acceptable carrier or excipient.

In another embodiment of the present invention, there is provided a method of pharmaceutical composition, comprising endostatin or fragments or derivatives, analogs thereof, a statin and a pharmaceutically acceptable carrier or excipient.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 1A-1B show that stroke causes an increase in brain Domain V levels. A Harlan Sprague Dawley rat was subjected to stereotaxic injection of endothelin-1 to occlude the middle cerebral artery (MCAo). The rat was anesthetized with ketamine and xylazine and after the skull was exposed and a small hole drilled on the left at stereotaxic coordinates +0.9 mm anterior, +3.4 mm lateral relative to bregma and at a depth of 8.5 mm from the dural surface, 3 ml of endothelin-1 (1 mg/ml, American Peptide Company, CA) was injected. FIG. 1A: Representative western blot for Domain V and GAPDH (loading control) from the stroked (2) and nonstroked (1) cerebral hemispheres from the same single rat, 7 days after stroke. The stroked cerebral hemisphere contained more ($p<0.0001$) Domain V (85 kDa band) and its LG3 (26 kDa band) component ($p<0.001$) than the unstroked hemisphere as normalized to GAPDH and analyzed via optical densitometry in FIG. 1B (DV shown).

FIG. 2A: Rat brain endothelial cells (8) routinely grown and passaged in a cell incubator (NuAire, Plymouth, Minn.) in Dulbecco's Modified Eagle Medium (DMEM) containing 10% fetal bovine serum, heparin 10 mg/ml, and acidic FGF 50 ng/ml, were added to Matrigel coated wells±pre-incubation with Domain V±function-blocking $\alpha 5\beta 1$ antibody (10 mg/ml) for 30 minutes. FIG. 2B: After 9 hours, Domain V treated cells formed more (**$p<0.0001$) tubes than controls which was in turn significantly blocked by anti-$\alpha 5\beta 1$ antibody (*$p<0.001$, compared to DV treatment). Error bars=s.d., n=3 experiments, HPF=high power field.

FIG. 7 shows that administered Domain V localizes to stroke and peri-infarct tissue by immunohistochemistry. Frozen tissue sections from stroked animals treated with Domain V or PBS vehicle control were processed via immunohistochemistry with antibodies directed against von Willebrand factor and the HIS epitope to visualize blood vessels and administered Domain V, respectively. There was an abundance of Domain V in stroked tissue and the stroke peri-infarct brain tissue. Here Domain V deposited in a perivascular distribution. In contrast, no Domain V was detected in the corresponding unstroked contralateral brain tissue of the same Domain V treated animal suggesting that Domain V specifically homes to stroked and peri-infarct brain tissue.

FIG. 9A: Frozen tissue sections were immunostained for the newborn neuronal marker doublecortin and the mean percentage of doublecortin positive pixels per high power field (HPF, 20 images per animal) in peri-infarct brain tissue of a PBS and Domain V treated animal was quantified with Adobe photoshop. Significantly more doublecortin pixels were detected in the animal treated with Domain V (*=$p<0.0001$). FIG. 9B: Immunohistochemistry of the Domain V treated animal showing several different doublecortin (green) positive neurons closely associated with peri-infarct blood vessels with closely associated administered Domain V as detected with anti-HIS antibody (red). Cell nuclei are counterstained with DAPI (blue).

FIG. 12A: BDNF ELISA of conditioned media from brain endothelial cells+/−Domain V+/−α5β1 (directed against α5 ligand binding domain) antibody+/−SNAKA51 (α5β1 activating antibody) over the course of 24 hours. This demonstrates that Domain V (**p=0.0025), α5β1 antibody (*p=0.0001) and SNAKA51 (#p=0.0007) all significantly increase BDNF levels. The simultaneous addition of α5β1 antibody and Domain V results in baseline BDNF release levels, while SNAKA51 and Domain V further increased BDNF levels, but this increase was not statistically significant (p=0.06). FIG. 12B: Representative BDNF western blot from ipsilateral stroke brain tissue in animals treated with PBS vehicle control or Domain V on post-stroke days 3 and 7.

FIGS. 13A-13H show that Domain V interacts with and exerts its pro-angiogenic effects via the α5β1 integrin. FIG. 13A: Quantification of representative brain endothelial cell adhesion assay to immobilized BSA (negative control) or Domain V+/−α5β1 function blocking antibody (10 mg/ml) demonstrating that Domain V supports significantly more cell adhesion as compared to BSA (** p=0.00005) which could be significantly inhibited by α5β1 function blocking antibody (*p=0.0007). FIG. 13B: α5β1-DV ELISA demonstrates that Domain V binds to immobilized α5β1 integrin in a dose dependent fashion with a Kd of approximately 30 nM. Tween 20 negative control also is shown. FIG. 13C: Quantification of cells migrating towards 3% fetal bovine serum (control) or DV+/−α5β11-GST or fibronectin-GST (as normalized to negative control (no chemotractant) demonstrating that Domain V was as powerful a chemotractant as 3% serum which could be significantly inhibited by α5β1-GST (* p=0.02) or fibronectin-GST (** p=0.01), error bars are standard deviation. FIG. 13D: Representative images of brain endothelial cells on matrigel after 12 hours, +/−Domain V+/− the α5β1 specific binding peptide CRRETAWAC (SEQ ID NO: 3) demonstrating that CRRETAWAC inhibits DV's enhancement of tube-like structure formation. FIG. 13E: Quantification of matrigel tube experiments in (FIG. 13D) demonstrating that Domain V significantly enhanced of tube-like structure formation (* p=0.0003) was significantly inhibited (** p=0.001) by CRRETAWAC. FIG. 13F: Representative α5β1 western blot of serum-starved confluent brain endothelial cells with GAPDH loading control over 8 hours+/−Domain V demonstrating that whole cell α5β1 levels diminish over 8 hours in controls while Domain V maintains α5β1 levels. FIG. 13G: α5β1 immunocytochemistry of brain endothelial cells demonstrating that Domain V exposure shifts α5β1 localization from even cellular distribution to surface/lamellipodia. FIG. 13H: Representative western blot of stroked (I) and contralateral (C) post-stroke day 3 brain tissue from PBS and Domain V treated animals with corresponding GAPDH loading control demonstrating a significant increase in total stroked brain α5β1 levels with Domain V treatment.

FIG. 14A: DV increases the proliferation of mouse brain endothelial cells, as compared to cell media control, which can be blocked by the addition of VEGF neutralizing antibody or α5β1 integrin function blocking antibody. FIG. 14B: Adding α2β1 integrin to the cells suppresses rather than increases the growth of the cells. Bars are mean values+/−standard deviation (FIG. 14B). **p<0.01. ##p<0.01.

FIG. 15A: In BALB/c strain [$^3$H]mannitol and [$^{14}$C] sucrose R$_{Tissue}$ values measured in the absence (0 hour control) and presence of DV (8 and 24 hours). The difference between the three experimental group for both [$^3$H]mannitol and [$^{14}$C]sucrose is not greater than would be expected by chance after allowing for the effects of differences in region (*P>0.05; Two Way ANOVA). Each group n=4. Values mean±SEM. FIG. 15B: In C57BI6 strain [$^3$H]mannitol and [$^{14}$C]sucrose R$_{Tissue}$ values measured in the absence (0 hour control) and presence of DV (2 hours). The difference between the experimental group for both [$^3$H]mannitol and [$^{14}$C]sucrose is not greater than would be expected by chance after allowing for the effects of differences in region (*P>0.05; Two Way ANOVA). Each group n=5. Values mean±SEM.

DETAILED DESCRIPTION OF THE INVENTION

Figure 2A:
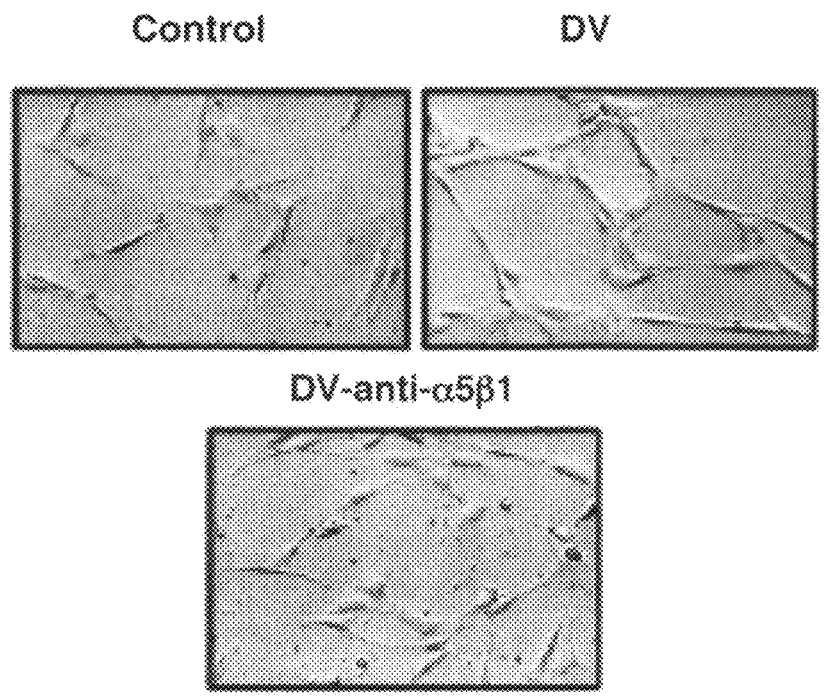
FIGS. 2A-2B show that Domain V enhances brain endothelial cell capillary tube formation.

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

The present invention provides a method of stimulating or enhancing angiogenesis in a patient comprising, administering to said patient a therapeutically effective amount of an endorepellin protein, wherein said endorepellin protein has an amino acid sequence of domain V of perlecan or fragments or derivatives, analogs thereof; and stimulating or enhancing generation of blood vessels. Preferably, fragments of the domain V of perlecan has an amino acid sequence that is at least 70%, 75%, 80%, 85%, 90% or 95% identical to domain V of perlecan. The domain V of perlecan or fragments or derivatives, analogs thereof may be administered by any useful method which could be readily determined by a person having ordinary skill in this art. Furthermore, the domain V of perlecan or fragments or derivatives, analogs thereof may be administered in an amount of from about 0.1 mg/kg to about 10 mg/kg of the patient's body weight. Typically, the administration results in brain endothelial cell capillary tube formation within the neurons and/or increased expression of the pro-angiogenic α5β1 integrin in brain endothelial cells.

The present invention also provides a method of stimulating or enhancing angiogenesis in a patient comprising, administering to said patient a therapeutically effective amount of an endostatin protein, or fragments or derivatives, analogs thereof; and stimulating or enhancing generation of blood vessels. Preferably, the fragments of endostatin has an amino acid sequence that is at least 70%, 75%, 80%, 85%, 90% or 95% identical to endostatin. Generally, a person having ordinary skill in this art would be able to readily derive useful fragments or derivatives. The endostatin or fragments or derivatives, analogs thereof may be administered by any useful method that could be readily determined by a person having ordinary skill in this art. Generally, the endostatin or fragments or derivatives, analogs thereof may be administered in an amount of from about 0.1 mg/kg to about 10 mg/kg of the patient's body weight. The administration results in brain endothelial cell capillary tube formation within the neurons.

The present invention also provides a pharmaceutical composition, comprising a domain V of perlecan or fragments or derivatives, analogs thereof, a statin compound and a pharmaceutically acceptable carrier or excipient.

The present invention also provides a pharmaceutical composition, comprising endostatin or fragments or derivatives, analogs thereof, a statin compound and a pharmaceutically acceptable carrier or excipient.

The present invention also provides a pharmaceutical composition, comprising endostatin or fragments or derivatives, analogs thereof, a statin and a pharmaceutically acceptable carrier or excipient.

The composition disclosed herein may be administered either alone or in combination with another drug or a compound. Such a drug or compound may be administered concurrently or sequentially with the composition disclosed herein. The effect of co-administration with the composition is to lower the dosage of the drug or the compound normally required that is known to have at least a minimal pharmacological or therapeutic effect against the disease that is being treated.

The composition described herein and the drug or the compound may be administered independently, either systemically or locally, by any method known in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The composition described herein and the drug or the compound may be administered independently one or more times to achieve, maintain or improve upon a therapeutic effect. It is well within the skill of an artisan to determine dosage or whether a suitable dosage of either or both of the composition and the drug or the compound comprises a single administered dose or multiple administered doses.

As is well known in the art, a specific dose level of such an composition generated thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

Administration of the composition of the present invention to a patient or subject will follow general protocols for the administration of therapies used in treatment of cerebral vascular disease or disorders taking into account the toxicity, if any, of the components in the composition and/or, in embodiments of combination therapy. It is expected that the treatment cycles would be repeated as necessary. It also is contemplated that various standard therapies, as well as surgical intervention, may be applied in combination with the described therapy.

As is known to one of skill in the art the composition described herein may be administered along with any of the known pharmacologically acceptable carriers. Additionally the composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Endothelial Cells

Human umbilical vein (HUVEC) and brain microvascular endothelial cells were purchased from Lonza (Basel, Switzerland) and Cell Systems (Kirkland, Wash.), respectively, and passaged as per the suppliers instructions. Mouse and rat brain microvascular endothelial cells were provided by Jane Welsh, Texas A&M University, and passaged as described (5).

EXAMPLE 2

Domain V and Endostatin

Human endostatin was purchased from Cell Sciences, Inc. (Canton, Mass.) and Sigma Chemical (St. Louis, Mo.). Domain V (DV) was cloned into the vector pSecTag2A (Invitrogen, Carlsbad, Calif.) and purified from transfected 293FT (ATCC, Manassas, Va.) cells via its C-terminal 6×His tag and Ni-ATA agarose beads (Qiagen, Valencia, Calif.) column chromatography. Dialyzed DV (against PBS) purity was confirmed via SDS-PAGE and western blot with anti-DV (R&D systems, Minneapolis, Minn.) and anti-his antibodies (EMD Chemicals, Gibbstown, N.J.). Thirty minute pretreatments with previously demonstrated anti-angiogenic concentrations of DV (250 nM) and endostatin (600 ng/ml) and heat inactivated controls (100° C. for 30 min) were used for all experiments. For all described experiments, N=15 (5 separate experiments, each condition performed in triplicate). Statistical significance ($p<0.05$) was determined for all experiments by Student's unpaired t-test with the Sigmastat software package.

EXAMPLE 3

Endothelin-1 Middle Cerebral Artery In Vivo Stroke Model

Harlan Sprague Dawley rats (n=10) were subject to middle cerebral artery occlusion stereotaxic surgery with endothelin-1 (American Peptide Company, Sunnyvale, Calif.) or PBS injection. Rats were terminated 3 or 7 days post surgery and brain tissue was processed for Domain V and GAPDH western immunoblot analysis.

EXAMPLE 4

In Vitro Angiogenesis Assays

Matrigel experiments were performed as described (7). After 12-18 hrs, cells were imaged and tube formation was quantified (tube pixels/high power field, 10 areas per condition) with Adobe Photoshop CS. Cell migration was assessed with a modified Boyden Chamber (NeuroProbe, Gaithersburg, Md.) following the instructions of the manufacturer. Migration across a type I collagen-coated polycarbonate membrane towards serum free media+/−3% fetal bovine serum was assessed after 6-8 hours. Proliferation was assessed after 48 hours in serum free media containing VEGF 20 ng/ml with MTS solution (Promega, Madison, Wis.) following the manufacturer's instructions.

EXAMPLE 5

Neuron-Brain Endothelial Cell Co-Culture Tubulogenesis Assay

Cerebellar granule neurons, isolated from postnatal day 8 rats, were added to a chamber slide pre-coated with laminin (Invitrogen) and grown overnight. Brain endothelialn cells were then added overnight followed by experimental treatments for 2-6 hours in serum-free media. Fixed cells were immunostained with anti-Von Willebrand factor, (Dako, Denmark) or anti-TUJ1 (Neuromics, Edina, Minn.) antibodies and appropriate fluorochrome-tagged secondary antibodies (Jackson ImmunoResearch, West Grove, Pa.) for confocal microscopy (Zeiss, New York, N.Y.).

EXAMPLE 6

Results

As peak peri-infarct angiogenesis initiates after 3-7 days, the stroked and nonstroked control cerebral hemispheres, from the same animal, were examined for Domain V levels by western immunoblot after 3 and 7 days after stroke (n=5 for each time point). Three days after stroke induction, a 530%±20% (standard deviation) increase in Domain V in the stroked cerebral hemisphere was demonstrated as normalized to GAPDH loading control and quantified by optical densitometry (ImageJ, NIH software) ($p<0.001$ by Student's unpaired t-test) (FIG. 1A-1B).

Figure 2B:
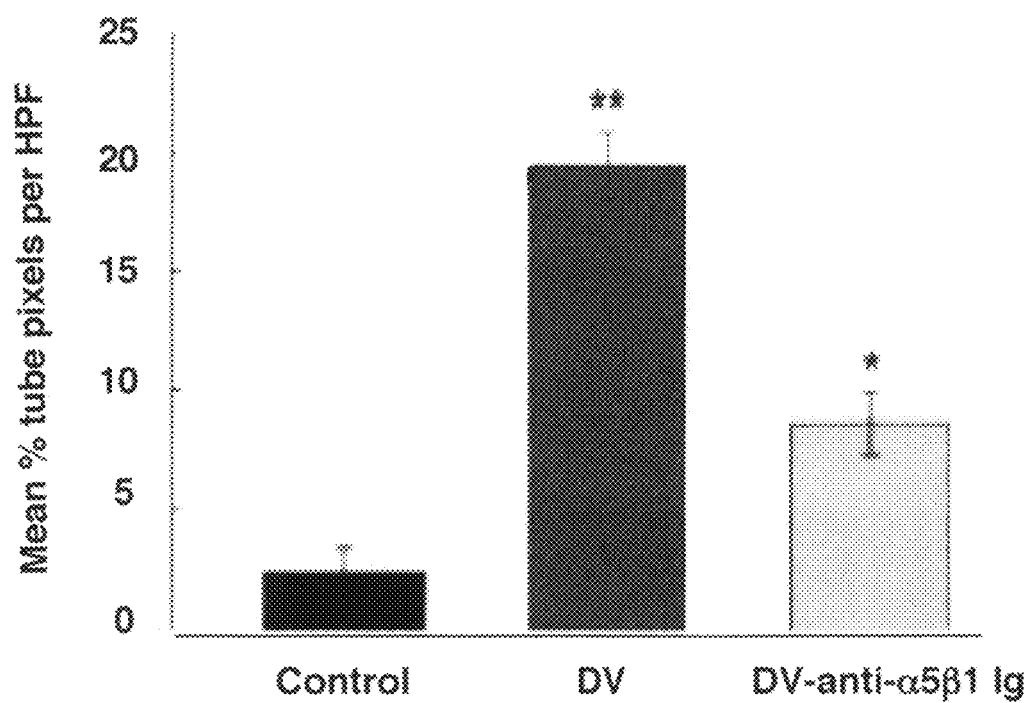

The ability of DV to affect brain angiogenesis, and the involvement of $\alpha5\beta1$ integrin in this process was examined using an in vitro capillary tube assay. Rat brain microvascular endothelial cells (50,000 cells/well, provided by Jane Welsh, Texas A&M) (8) were added to Matrigel (a vascular basement membrane-like substance that stimulates capillary tubulogenesis (9), 25 ml/well, BD Biosciences) coated wells of a 24 well plate±a pre-incubation with DV (200 nM)±function-blocking $\alpha5\beta1$ antibody (10 mg/ml, FIG. 2A). After 9 h, DV treated brain endothelial cells formed significantly more capillary tubes as compared to untreated controls ($p<0.0001$). This effect was in turn significantly blocked by anti-$\alpha5\beta1$ antibody ($p<0.001$, as compared to DV treatment alone, FIG. 2B). Pre-treatment with anti-$\alpha5\beta1$ blocking antibody alone did not significantly affect tube formation (p=0.3).

Figure 3:
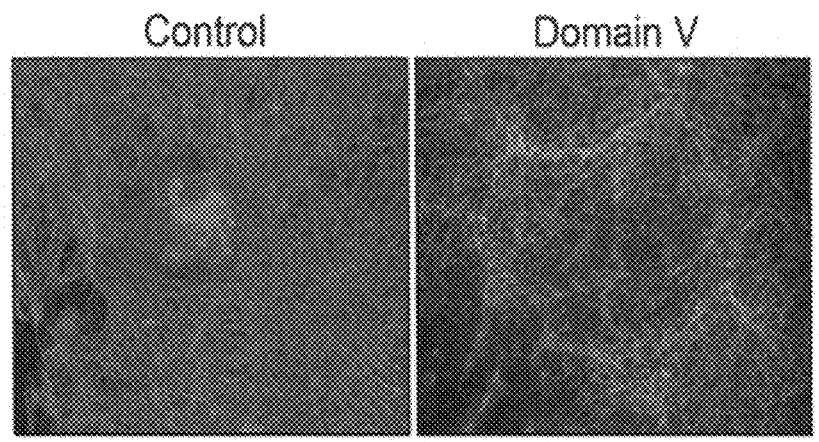
FIG. 3 shows that Domain V stimulates brain endothelial cell capillary formation and interaction with neurons. Rat brain endothelial cells (red, stained with anti-von Willebrand factor antibody, Dako) were added to a layer of cerebellar granule neurons (green, stained with an anti-TUJ1 antibody, Dako) and then treated with Domain V (300 nM) or vehicle control. In the control, endothelial cells segregated from neurons forming distinct islands, while Domain V treatment resulted in capillary tube formation around the neurons.

Next, to determine whether DV could affect the interaction between brain endothelial cells and neurons, i.e. the neurovascular niche, a brain endothelial cell granule neuron co-culture assay was developed in which brain endothelial cells are added to a layer of primary neurons obtained from a postnatal day 8 rat cerebellum which yielded a >95% pure newly generated granule neuron culture (10). The neurons ($5\times10^4$ cells/well) were added to an 8 chamber well slide pre-coated with laminin and allowed to grow overnight at 37° C. The following day, brain endothelial cells were added ($3\times10^4$ cells/well) and allowed to grow overnight followed by treatment with DV for 6 hours in serum free media. In this assay, brain endothelial cells rapidly (within 2-3 h) segregate from the neurons forming distinct endothelial cell islands. DV treatment resulted in dramatic brain endothelial cell capillary tube formation within the neurons (FIG. 3).

Figure 4:
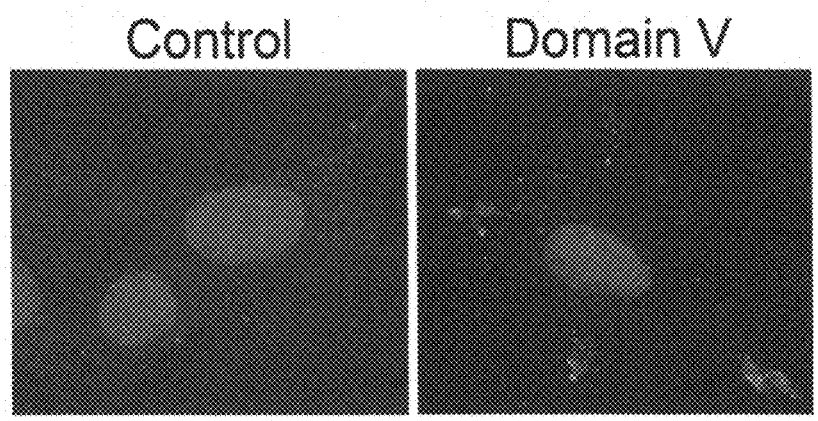
FIG. 4 shows that Domain V causes $\alpha 5\beta 1$ integrin redistribution. Brain endothelial cells on laminin were treated with Domain V (300 nM) or vehicle control for 2 hours. The cells were then fixed, and immunostained for $\alpha 5\beta 1$ integrin (green), and DAPI nuclear counterstain (blue) and visualized by confocal microscopy. Domain V treatment resulted in $\alpha 5\beta 1$ redistribution from to cell surface projections commonly seen in angiogenic endothelial cells.

To demonstrate whether Domain V affects the expression of the pro-angiogenic $\alpha5\beta1$ integrin in brain endothelial cells, the subcellular localization of $\alpha5\beta1$ integrin in untreated and Domain V exposed cultured rat brain endothelial cells were analyzed via immunocytochemistry and confocal microscopy. FIG. 4 shows that DV treatment resulted in a redistribution of $\alpha5\beta1$ integrin from diffusely cytoplasmic to cell surface projections commonly seen in angiogenic endothelial cells.

Figure 5:
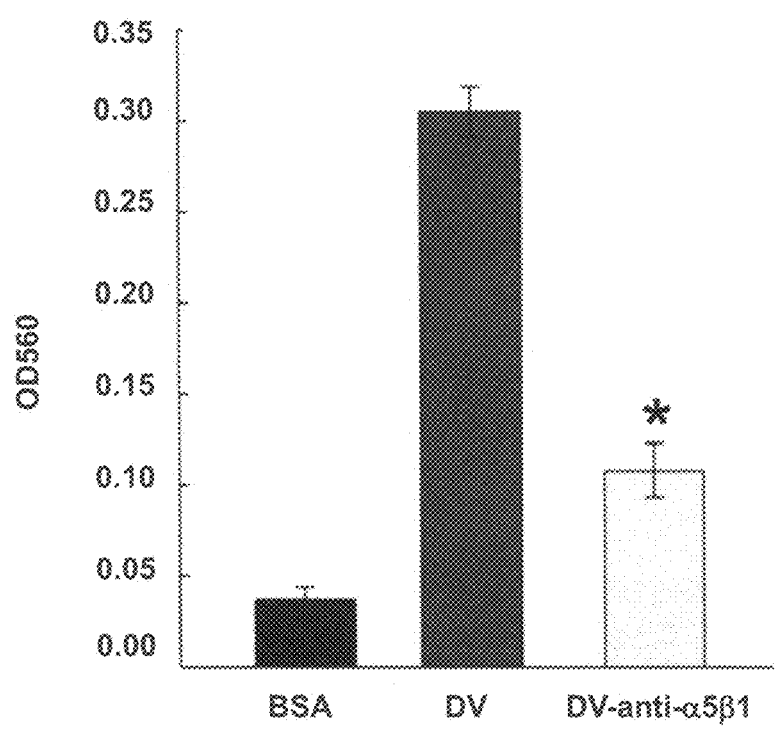
FIG. 5 shows that Domain V supports brain endothelial cell adhesion. Brain endothelial cells±pre-incubation with $\alpha 5\beta 1$ function blocking antibody were added to wells coated with 1% BSA or Domain V, followed by fixation, staining and OD560 spectrophotometry. Significantly more (#, $p<0.001$) brain endothelial cells adhered to Domain V than BSA which was in turn significantly (*, $p<0.001$) inhibited by the addition of $\alpha 5\beta 1$ function blocking antibody. n=3. Error bars=s.d.

To determine whether Domain V could support brain endothelial cell adhesion via the $\alpha5\beta1$ integrin, a cell adhesion assay was performed with wells coated with 1% BSA (adhesion control) or Domain V (40 micrograms/ml) and added cells±$\alpha5\beta1$ function-blocking antibody (10 micrograms/ml) pre-incubation. FIG. 5 demonstrates that Domain V supported significantly more brain endothelial cell adhesion than BSA ($p<0.001$) and that $\alpha5\beta1$ function blocking antibody significantly ($p<0.001$) inhibited brain endothelial cell adhesion to DV, suggesting the possibility that DV can support $\alpha5\beta1$ integrin mediated brain endothelial cell adhesion.

These results demonstrate that brain Domain V is increased post-stroke and enhances both angiogenesis in a neuronal milieu and the interaction between brain endothelial cells and neurons. Furthermore, these effects require interactions with the $\alpha5\beta1$ integrin. Importantly, these results support the position that the post-stroke brain self-repairs by generating a bioactive fragment (DV) of perlecan and one can therapeutically exploit this brain repair mechanism.

EXAMPLE 7

DV Effects on Brain Angiogenesis and Formation of the Neurovascular Niche

To demonstrate the role of Domain V in brain angiogenesis in vitro, angiogenesis assays are performed including Matrigel capillary tube assays, cell migration assays, and cell proliferation assays with microvascular brain endothelial cells and human recombinant Domain V. A neuron-brain endothelial cell co-culture capillary tube assay is used to study the effects of Domain V on capillary tube formation in a more brain-like environment as well as to study the formation of the neurovascular niche. The above studies are performed in an oxygen and glucose-deprived environment (OGD) to model focal ischemia in vitro. DV will significantly, and in a dose-dependent fashion, enhance brain angiogenesis as well as the interaction between neurons and endothelial cells in both normal and OGD conditions.

EXAMPLE 8

DV Cloning and Purification

Domain V was cloned into the pSecTag2A vector (Invitrogen) which added a 6×His tag to the C-terminus of DV. Plasmids were transfected into 293FT (ATCC, Manassas, Va.) cells via Lipofectamine (Invitrogen). After transfection, serum-free conditioned media (containing cell secreted DV) was collected and DV was purified via Ni-ATA agarose bead column chromatography at 4° C. The eluted DV was dialyzed against 1×PBS and assessed for purity via SDS-PAGE stained with Brilliant Blue G-colloidal ($DV_C$) and by western blot ($DV_{WB}$) analysis with anti-DV antibody (shown), and anti-His antibody. The DV was quantified with Quick Start Bradford Dye Reagent.

EXAMPLE 9

DV Effects on Endothelial Cell Proliferation

Endothelial cell proliferation is an important initial step in angiogenesis. To assess the proliferative effects of Domain V on endothelial cells, microvascular brain endothelial cells from both mice and rats are used to both rule out species-specific differences and correspond with the use of rats in in vivo stroke model. Human umbilical vein endothelial cells (HUVEC, Lonza, Basel, Switzerland) are used as a control, and human brain microvascular endothelial cells (Cell Systems, Kirkland, Wash.) are used to determine whether Domain V effects might also be applicable to humans. For proliferation assays, the cells are harvested with trypsin 0.25% (Invitrogen), pretreated with vehicle control or different concentrations of DV (1-450 nM concentrations used for all in vitro angiogenesis experiments) in suspension for 30 minutes in serum free media containing 20 ng/ml VEGF, and then are added to 96 well plates at a density of $5×10^3$ cells/well. The cells are then incubated for 48 h under normal growth conditions. MTS solution is then added (20 ml/well) for 1 h followed by an absorbance reading at 490 nm with the plate reader.

EXAMPLE 10

Determination of DV Effects on Endothelial Cell Migration

As angiogenic endothelial cells are proliferating, they begin to migrate towards a tissue region requiring a new blood supply in response to a chemoattractant released by the blood vessel demanding tissue. To assess whether DV could affect endothelial cell migration, the cells are harvested and loaded into the upper chamber of a modified Boyden Chamber (NeuroProbe, Gaithersburg, Md.)±preincubation for 30 minutes in the appropriate serum-free media with different concentrations of DV in suspension at 37° C., and allowed to migrate across a polycarbonate membrane coated with type I collagen, laminin or fibronectin towards serum free media+/−3% FBS in the lower chamber for 6-8 h at 37° C. Importantly, these extracellular matrices represent a brain endothelial cell neutral, anti-angiogenic and pro-angiogenic substrate (11), respectively, and their use should allow one to determine if DV effects are ECM specific. The membrane (containing migrating cells) are then fixed with acetone, and the cells stained with crystal violet (Sigma) and counted under the microscope. Additionally, whether DV differentially affects migration towards different chemoattractants including VEGF, brain derived neurotrophic factor (BDNF), nerve growth factor (NGF) and basic FGF (bFGF) is determined.

EXAMPLE 11

Determination of DV Effects on Endothelial Cell Matrigel-Induced Tubulogenesis

Once endothelial cells arrive at the intended tissue target requesting a new blood supply, the cells undergo capillary morphogenesis to make the new blood vessel. Matrigel tubulogenesis assays are a well established technique to study endothelial cell capillary morphogenesis in vitro (12). To that end, these assays are performed as described above±endothelial cell pre-incubation with different concentrations of DV. Cells are observed at various time points and then fixed in 4% paraformaldehyde after 12-18 h. Images are acquired with a CCD camera attached to an inverted microscope using standard image capturing software. Tube formation is quantified (tube pixels/microscopic field, 10 fields per condition) with Adobe Photoshop CS.

EXAMPLE 12

Determination of DV Effects on Endothelial Cell Tubulogenesis and Neuronal Interactions in Co-Culture To investigate the ability of Domain V to modulate brain endothelial cell capillary tube formation in a more brain-like environment than Matrigel, a co-culture assay system made up of cerebellar granule neurons and brain endothelial cells was developed. The postnatal day 8 rat cerebellum was selected as the neuronal source as it is easily accessible and an abundant source of newly born neurons (13), whose interaction with brain endothelial cells. In addition to laminin, the neurons are added to wells pre-coated with collagen I or fibronectin to determine the relative importance of each underlying substrate to endothelial cell tube formation. The effects of different concentrations of Domain V on the extent of endothelial cell tube formation is determined for different incubation periods (1, 3, 6, 9 hours). Domain V dose dependent enhancing effects on tube formation is demonstrated.

The data herein suggests that in the absence of Domain V, brain endothelial cells segregate from the neurons while Domain V promotes capillary tube formation amongst the neurons. Therefore, in addition to studying capillary formation, this co-culture system allows one to examine DV's effects on the dynamic interactions between endothelial cells, neurons and the ECM. First, the confocal microscope is used to examine the effects of Domain V at different time points on the 3 dimensional interaction between the brain endothelial cells, neurons and surrounding ECM by collecting Z-stack images of fixed cells immunostained for anti-Von Willebrand Factor, anti-TUJ1, anti-$\alpha5\beta1$, the tight junction protein claudin-5 and anti-ECM components including fibronectin, laminin and type IV collagen. In these studies, whether DV affects the endothelial cell distribution of $\alpha5\beta1$ integrin in relation to the surrounding ECM as well as determines changes in endothelial cell homotypic interactions, as measured by changes in claudin-5 expression and cellular distribution, and heterotypic neuronal interactions, as measured by changes in endothelial cell-neuron proximity, is shown.

Live cell microscopy (Nikon microscope with motorized stage and heated, $CO_2$ stage connected to a CCD camera and PC with Metamorph imaging software) is used to image the interaction of diI and diO fluorescently labeled neurons and endothelial cells (14), respectively±DV therapy over a prolonged period. Domain V treatment increases the visible physical contacts between the brain endothelial cells and neurons, thus promoting and enhancing the neurovascular niche formation during stroke recovery. Endothelial cell-neuron contact are quantified as the number of visible endothelial cell-neuron contacts per microscopic field/per hour. The extent that individual endothelial cells contact neurons per hour is also quantified.

Finally, to determine whether the presence of neurons or their secreted ECM/growth factors is necessary for DV's capillary tube promoting effects, in some experiments the neurons are removed with Cellstripper, a non-enzymatic dissociation solution, which will leave the neuron secreted matrix on the well bottom as verified by ECM antibodies, prior to the addition of the brain endothelial cells±DV treatment. In other experiments, neuronal conditioned media is added to the endothelial cells cultured on laminin. The data shows the necessity of the neuron-endothelial cell interactions for endothelial cell tube formation.

EXAMPLE 13

Effects of Oxygen-Glucose Deprivation (OGD) in DV In Vitro Assays

The effects of Domain V in an in vitro model of ischemia (15) are shown using the above described angiogenesis assays in reduced glucose media (1 g/L) in a hypoxia chamber. For each assay, the cultures, in reduced glucose media±DV, are placed in the hypoxia chamber which are flushed with 95% $N_2$/5% $CO_2$ for 1 h, followed by chamber sealing for the experiment duration as described above for each angiogenesis assay. OGD alone increases brain endothelial cell angiogenesis and that this is further enhanced by DV.

EXAMPLE 14

α5β1 Integrin and DV Pro-Angiogenic Effects In Brain Endothelial Cells

Requirement of α5β1 for DV's pro-angiogenic effects means that α5β1 blockade and/or α5β1 reduction mitigates or inhibits Domain V pro-angiogenic effects. Therefore, the effects of functional inhibition of α5β1 integrin with a function blocking antibody and IgG control (Millipore, 10-20 mg/ml pre-incubated with cells) and reduction in α5β1 levels with siRNA (Accell pre-designed siRNA, Dharmacon, Chicago, Ill.), respectively, on DV and untreated brain endothelial cells in migration, proliferation and tubulogenesis assays are shown. α5β1 knockdown is confirmed via western blot.

EXAMPLE 15

Determination of DV Effects on Endothelial Cell α5β1 Surface Localization

To directly measure brain endothelial cell α5β1 integrin surface localization in response to DV exposure, the methods of Milner et al. (15) are used to prepare cells grown on plastic or various substrates (laminin, collagen, fibronectin or immobilized DV, at 40 mg/ml added to the wells overnight at 4° C.)±DV exposure for flow cytometry using the Becton-Dickinson FACSCalibur machine with CellQuest (Becton-Dickinson) ModFit LT (Verity) software.

EXAMPLE 16

Determination of DV Interaction and Activation of α5β1 Integrin

DV should bind to and activate the α5β1 integrin resulting in increased brain endothelial cell affinity for fibronectin via the RGD fibronectin/α5β1 binding motif. DV effects to increase brain endothelial cell adhesion to immobilized fibronectin and the RGD sequence GRGDS (SEQ ID NO: 1) versus a control peptide SDGRG (SEQ ID NO: 2) is shown.

Cell adhesion assays ware carried out as described above in wells coated with DV (40 micrograms/ml), fibronectin (10 micrograms/ml), GRGDS or SDGRG peptides (0.1 micrograms/ml), or 1% BSA. To show that cell adhesion to DV is α5β1-dependent, adhesion studies are conducted where function or expression of α5β1 is inhibited. Cells are treated with α5β1 siRNA following the instructions of the manufacturer and α5β1 knockdown efficiency is confirmed via western immunoblot. Alternatively, cells are pre-incubated with the anti-α5β1 blocking antibody prior to the adhesion assay. That inhibition of function or expression of α5β1 decreases or inhibits brain endothelial cell adhesion to DV is shown. That DV enhances brain endothelial cell adhesion to fibronectin and GRGDS peptide and α5β1 siRNA treatment inhibits brain endothelial cell adhesion to immobilized Domain V and that added DV enhances brain endothelial cell adhesion to fibronectin and GRGDS is shown.

EXAMPLE 17

Stroke-Generated DV

DV is administered post-stroke and its effects on stroke pathology and functional recovery are shown. Post-stroke angiogenesis is increased after DV administration in an in vivo stroke as is neurovascular niche formation, and pathologic and functional stroke outcomes in rats are improved. DV therapy is well tolerated in animals.

EXAMPLE 18

Endothelin-1 In-Vivo Stroke Model and DV Therapy

Harlan Sprague Dawley rats are subjected to endothelin-1 (or PBS sham control) induced middle cerebral artery occlusion (MCAo) as described above. Blood flow interruption is confirmed using a laser Doppler flowmeter (model BPM2, Vasamedics Inc, St. Paul, Minn.) (16) (49). 24 h after MCAo, the animals are randomized into two groups, 1 receiving 2-6 mg/kg of filtered DV (an amount sufficient to inhibit tumor angiogenesis as published (7)) by intraperitoneal (I.P.) injection (treated group) and 1 receiving vehicle control every 2 days for 2 weeks. Also starting at 24 h post MCAo, the rats receive daily (for 14 days) I.P. injections of bromodeoxyuridine (BrdU; 100 mg/kg; Sigma) to label newly synthesized DNA to identify newborn neurons in the recovering rat brains.

EXAMPLE 19

Stroke Tissue Immunohistochemistry and Western Immunoblot

To assess post-stroke angiogenesis and neurovascular niche formation±DV therapy in the rats, fresh brain tissue from stroked and sham stroked animals are frozen in liquid nitrogen. For angiogenesis immunohistochemistry, cryosections of the stroked cerebral hemispheres, obtained with a Microm HM 550 cryostat (Walldorf, Germany) are probed with antibodies directed against blood vessel antigens, i.e., CD31 and von Willebrand factor (Dako). The extent of blood vessel interactions with BrdU+ neurons are assessed and quantified with Adobe Photoshop CS. Furthermore, stroke tissue uptake and distribution of injected DV is shown with antibody directed to DV's 6×HIS tag (EMD). As compared to untreated stroked animals DV therapy will result in an increase in blood vessel, i.e., an increase in CD31 and/or von Willebrand positive cells, around stroked brain tissue that may also have increased α5β1 integrin expression and increased interaction between these blood vessels and BrdU+ neurons. Administered DV will localize to the stroke site and result in reduced infarct size.

EXAMPLE 20

Perlecan Domain V Therapy for Stroke-Induced Cerebral Palsy

Perinatal arterial ischemic stroke (PAS), a cerebrovascular event occurring during fetal or neonatal life, is a major cause of infantile cerebral palsy. Unfortunately, PAS is typically diagnosed retrospectively, i.e. after the damage has been done and too late for traditional stroke therapies such as tissue plasminogen activator. Therefore, successful cerebral palsy therapies should exploit brain self-repair mechanisms. Unfortunately, brain self-repair is poorly understood but appears to occur in a neurovascular niche of revascularization (angiogenesis) and neuronal repopulation (neurogenesis). Both of these processes involve protease-driven extracellular matrix (ECM) remodeling with unknown consequences. Post-stroke brain angiogenesis and neurovascular niche formation is stimulated in part by generating a bioactive fragment of the ECM, perlecan, and that this self-repair mechanism is exploited for PAS-induced cerebral palsy therapy. Stroke rapidly generates bioactive fragments of perlecan, which is the most protease-sensitive ECM component studied, and perlecan is required for both angiogenesis and neurogenesis. Furthermore, a perlecan fragment, domain V (DV, also known as endorepellin), can inhibit angiogenesis in nonbrain systems through the $\alpha 2\beta 1$ integrin.

The present invention shows that DV is upregulated in the brain after stroke and unexpectedly enhances brain angiogenesis in vitro and in vivo after stroke, possibly due to the absence of $\alpha 2\beta 1$ integrin in brain endothelial cells. DV exerts its effects in brain endothelial cells through the pro-angiogenic $\alpha 5\beta 1$ integrin, and enhances the interaction between neurons and endothelial cells. Collectively, these results suggest that the brain could self-repair through DV production and that this can be exploited therapeutically.

Figure 6A:
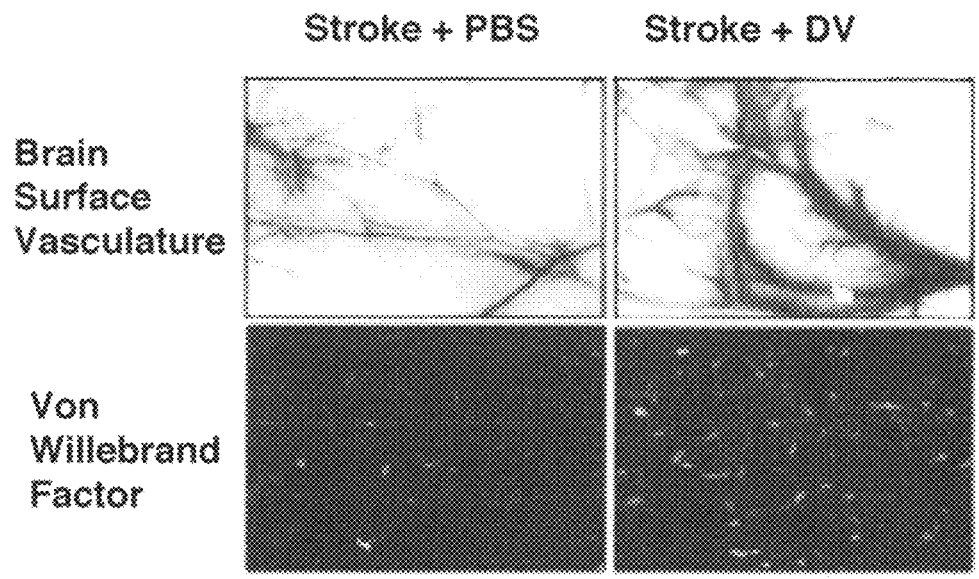
FIGS. 6A-6B show that Domain V treatment after perinatal arterial ischemic stroke (PAS) increases brain surface and stroke penumbral vasculature. Transient middle cerebral artery occlusion in 7 day old rats was induced via stereotactic injection of endothelin-1. The animals then received 0.5 mg/kg intraperitoneal injection of sterile filtered Domain V or PBS vehicle control 24 and 72 hours after stroke. After 5 days post-stroke, the animals' brains were removed and stroked brain surface vasculature was imaged, followed by von-Willebrand immunohistochemistry of frozen tissue sections to analyze penumbral vasculature. Domain V treatment resulted in brain surface hypervascularity and a significant ($p<0.001$) increase in stroke penumbral vasculature.
Figure 6B:
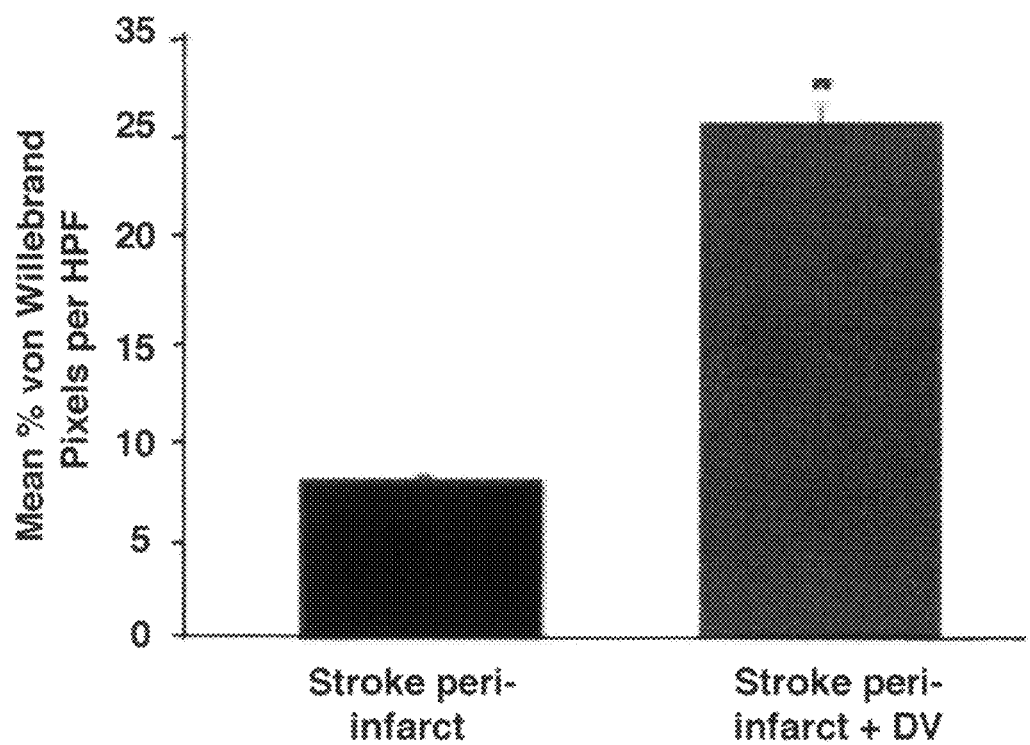

To demonstrate the utility of DV therapy for PAS, endothelin-1 was used to induce transient middle cerebral artery occlusion (MCAo) strokes in 7 day old rats. The animals then received 0.5 mg/kg intraperitoneal injection of sterile DV or PBS vehicle control 24 and 72 hours after stroke. As peak penumbral (the area immediately surrounding the stroked tissue) angiogenesis initiates after 3-7 days, the vasculature of the stroked brains was examined 5 days after stroke. There was hypervascularity on the surface of the stroked cortex in DV treated animals which was not evident on the contralateral cortex or in PBS treated stroked animals (FIGS. 6A-6B). Furthermore, immunostaining of frozen tissue sections of these brains with the blood vessel marker von-Willebrand factor revealed significantly increased stroke penumbral vasculature in DV treated animals as compared to PBS treated control (FIGS. 6A-6B). Collectively, these results suggest that DV could increase post-PAS angiogenesis.

EXAMPLE 21

Administered DV Localizes to Stroke and Peri-Infarct Tissue

Figure 8:
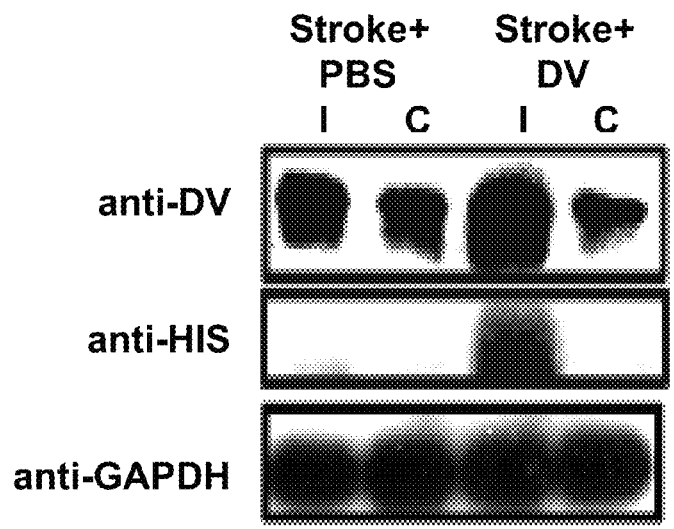
FIG. 8 shows that administered Domain V localizes to stroke brain tissue by western immunoblot. Lysate of the stroked ipsilateral (I) brain tissue or corresponding contralateral (C) nonstroked tissue from a PBS or Domain V treated animal was analyzed by western immunoblot with antibodies to Domain V (detects both endogenous and administered DV), HIS (detects only administered Domain V) and GAPDH protein loading control. The 85 kDa band is shown for anti-Domain V and anti-HIS. Significantly more Domain V was detected in the stroked tissue as compared to the contralateral tissue, when normalized to GAPDH loading control, in both the PBS ($p<0.001$) and Domain V ($p<0.00001$) treated animals, the latter even more so due to the extra administered Domain V. Administered Domain V as detected by anti-HIS antibody could only be detected in the lysate from the stroked cortex of the animal treated with Domain V.

Brain tissue was analyzed by immunohistochemistry to detect administered DV (HIS epitope tag on c-terminus of recombinant DV) as well as blood vessels (von Willebrand factor) to determine if administered DV could be detected in stroked brain tissue and where it might localize. FIG. 7 demonstrates that administered DV could be found in abundance in stroked brain tissue and to a lesser extent in the peri-infarct cortex, but not in the contralateral unstroked cortex of the same animal. Furthermore, virtually all of the administered DV deposited in a perivascular distribution in the peri-infarct cortex and the stroked tissue to a lesser extent, consistent with its brain blood-vessel promoting effects and its ability to target activated solid tumor perivasculature in vivo. Importantly, this suggests that DV is able to cross the blood brain barrier, at least as far as abluminal perivascular regions, via an as yet unknown mechanism, where it could be exposed to and exert effects on other cell types such as astrocytes and neurons. FIG. 8 demonstrates a similar result by western blot analyses of lysates obtained from the stroked and contralateral cortex of a PBS and DV treated stroked animal, respectively.

EXAMPLE 22

Administered DV Localizes to Stroke and Peri-Infarct Tissue

Figure 9A:
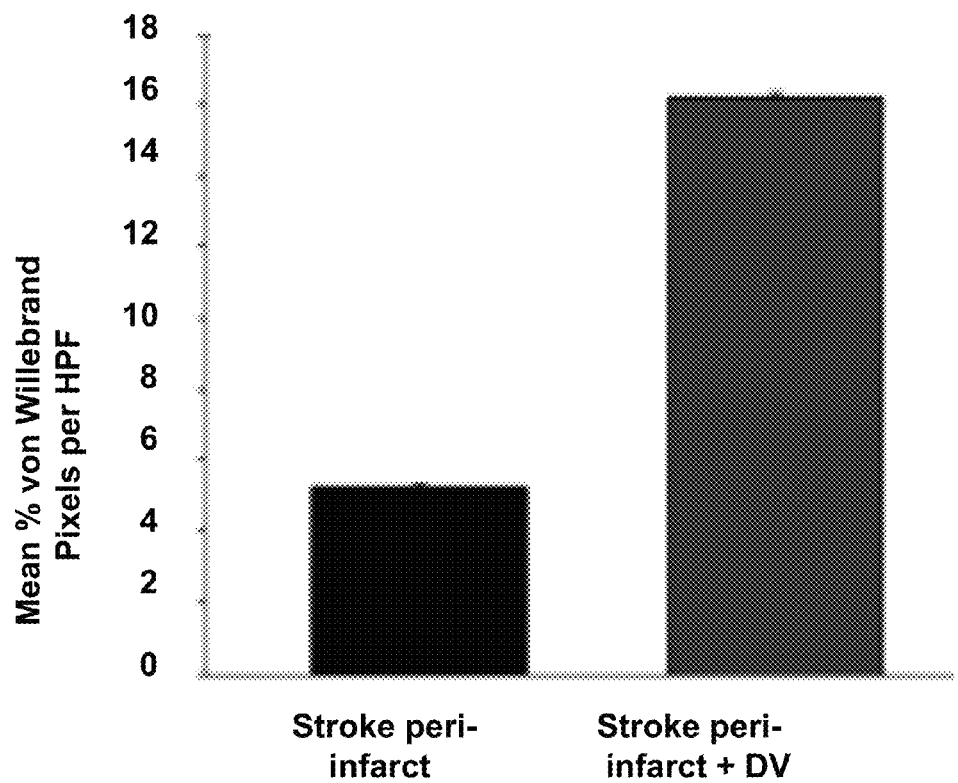
FIGS. 9A-9B show that Domain V treatment increases the number of newly born neurons in peri-infarct brain tissue.
Figure 9B:
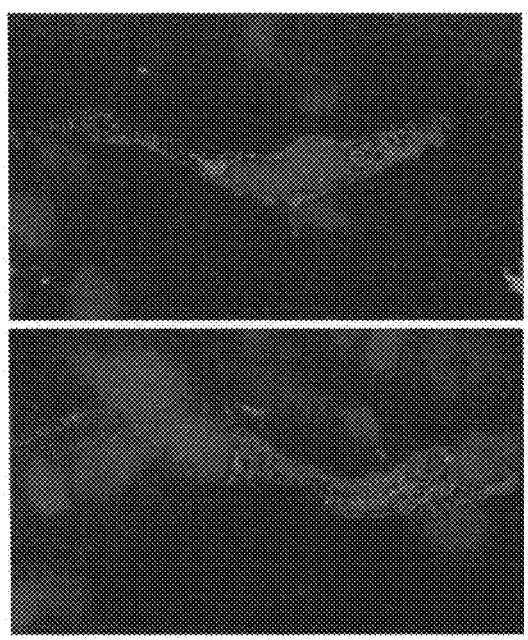

To determine whether DV therapy could affect the extent of neuroblasts migrating in the peri-infarct brain tissue, as defined as a brain area immediately adjacent to infarcted brain tissue, and thereby influence the repopulation of stroked brain tissue with new neurons, doublecortin immunohistochemistry was used (FIG. 9A) of brain sections from a PBS and DV treated stroked animal and quantified the mean number of doublecortin pixels per high power field (HPF, n=20 images per animal) in the respective stroke peri-infarct tissue. A significant increase in doublecortin positive pixels in the DV treated animal was noted. Furthermore, in seeming agreement with the hypothesis that DV fosters formation of the neurovascular niche, a significantly ($p<0.001$) greater percentage of identified doublecortin positive cells was noted in the immediate proximity to blood vessels, as identified by antibodies directed to von Willebrand antibody or HIS antibody (FIG. 9B) in the DV treated animal (90%+/−5%, n=20 images per animal) as compared to the PBS treated control (60%+/−3%) in the peri-infarct brain tissue.

EXAMPLE 23

DV Enhances Cortical Neuronal Migration In Vitro

By fostering formation of the neurovascular niche through effects on brain endothelial cells, as suggested by the results above, DV could be neuroprotective, enhance neurogenesis and neuronal migration. Furthermore, if DV crosses the blood brain barrier, it could also have direct effects on neurons. Whether DV could have direct neuronal effects that might be consistent with its therapeutic potential for stroke was determined. To that end, mouse primary cortical neurons from embryonic day 15 C57BI6 mice was isolated using routine sterile dissection technique for primary cell isolation paying particular attention to remove meninges and an in vitro migration assay was performed with these cells.

Figure 10:
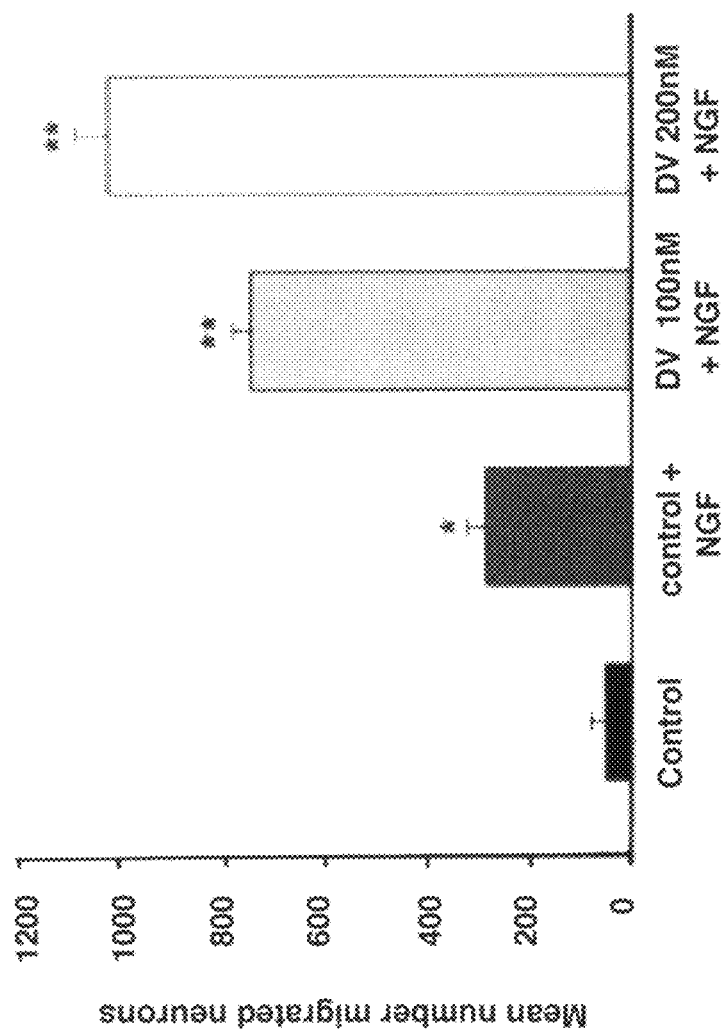
FIG. 10 shows that Domain V enhances cortical neuron migration. Cortical neurons from embryonic day 15 C57Bl6 mice+/−preincubation for 30 minutes with 100 nM or 200 nM Domain V were added to the upper well of a modified Boyden chamber ($3 \times 10^3$/well) and allowed to migrate for 8 h (at 37° C.) across a polycarbonate membrane coated with type I collagen towards a bottom well containing nothing (migration control) or nerve growth factor (NGF, 4 nM per well). N=3 for each condition. Domain V preincubation significantly, and a dose dependent fashion, enhanced cortical neuronal migration suggesting that it could have direct, potentially therapeutic effects on neurons. *=$p<0.001$, **=$p<0.0001$. Bars are standard error.

Prior to use, the neuronal identity was confirmed with TUJ-1 immunocytochemistry. A modified Boyden chamber (NeuroProbe, Gaithersburg, Md.) in which the neurons ($3\times10^3$/well) were loaded into the upper chamber±preincubation for 30 minutes in the appropriate serum-free media with 100 nM or 200 nM DV in suspension at 37° C., and then allowed to migrate across a polycarbonate membrane coated with type I collagen toward the chemoattractant nerve growth factor (NGF, 4 nM per lower well) for 8 h at 37° C. The membrane (containing migrating cells) was then fixed with acetone, and the cells stained with crystal violet (Sigma) and counted under the microscope. FIG. 10 shows that DV enhances cortical neuron migration by demonstrating that DV treatment significantly, and in a dose dependent fashion, enhanced cortical neuronal migration towards NGF (p<0.0001 for both DV concentrations), suggesting that DV could have direct, therapeutic effects on neurons.

DV Therapy Improves Functional Stroke Outcome

Figure 11:
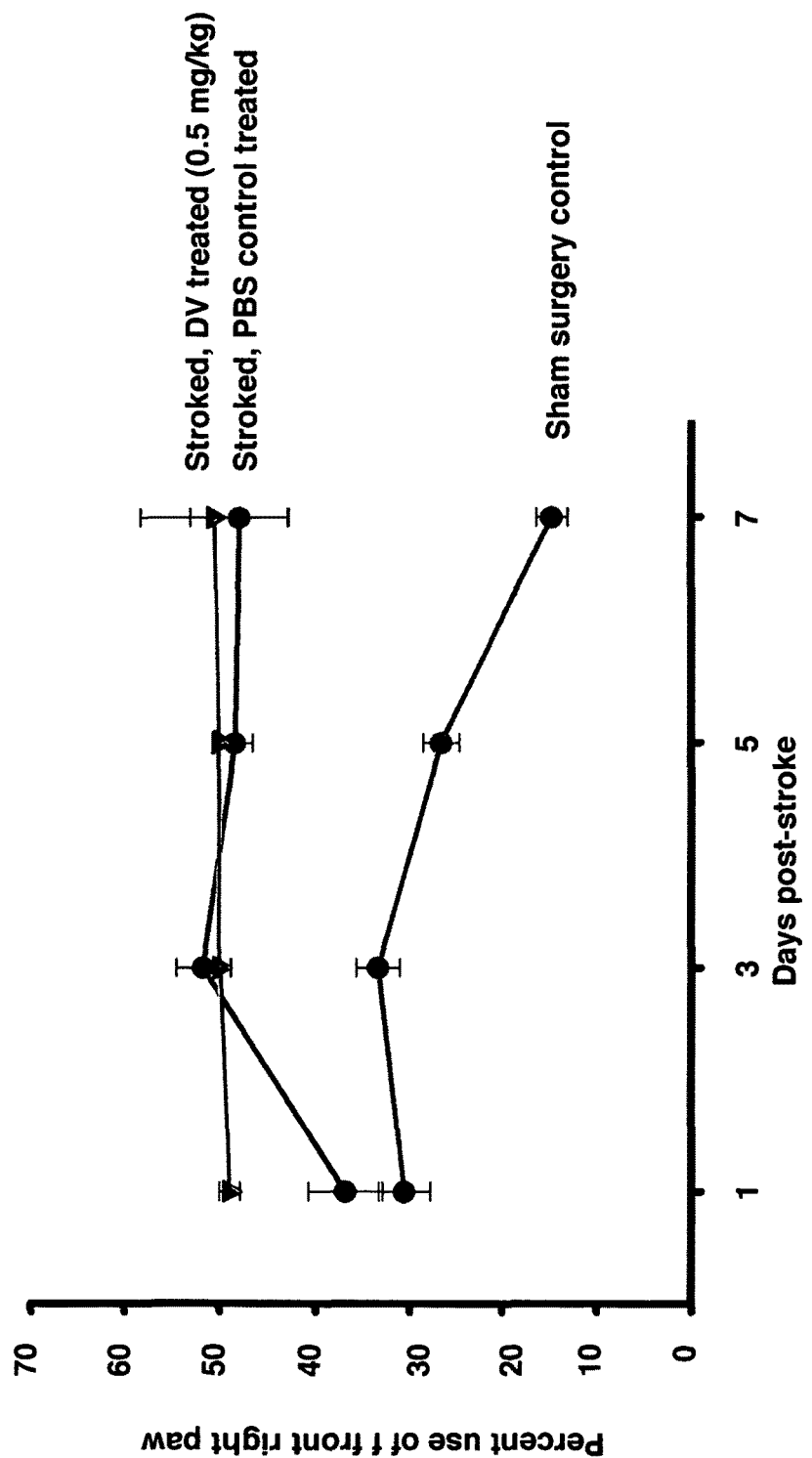
FIG. 11 shows that Domain V improves functional/motor outcome in the endothelin-1 animal stroke model. Stroked animals or sham surgery controls were placed in a 20 cm diameter×35 cm high transparent cylinder for 3 min to test limb preference and their ability to support weight on either forelimb (6). As the animal rears to explore the environment the number of bilateral paw placements, placements of the paw ipsilateral to the lesion (right), and placements of the paw contralateral to lesion (left) are counted. Paw contacts were videotaped and analyzed later. The percent of ipsilateral limb use was calculated using the equation ipsilateral contacts/ (ipsilateral+contralateral contacts)×100. N=5 per treatment group, *p<0.05, **p<0.001 comparing stroked Domain V treated and stroked PBS treated. From post-stroke day 3 onward, there was no statistical difference between sham controls and Domain V treated stroked animals. Domain V treated animals were treated with 0.5 mg/kg on post-stroke days 1, 3, 5, 7.

FIG. 11 shows that from post-stroke day 3 onward, there was no statistical difference between sham controls and Domain V treated stroked animals. Domain V treated animals were treated with 0.5 mg/kg on post-stroke days 1, 3, 5, 7.

EXAMPLE 24

Domain V Induces BDNF Release

Figure 12A:
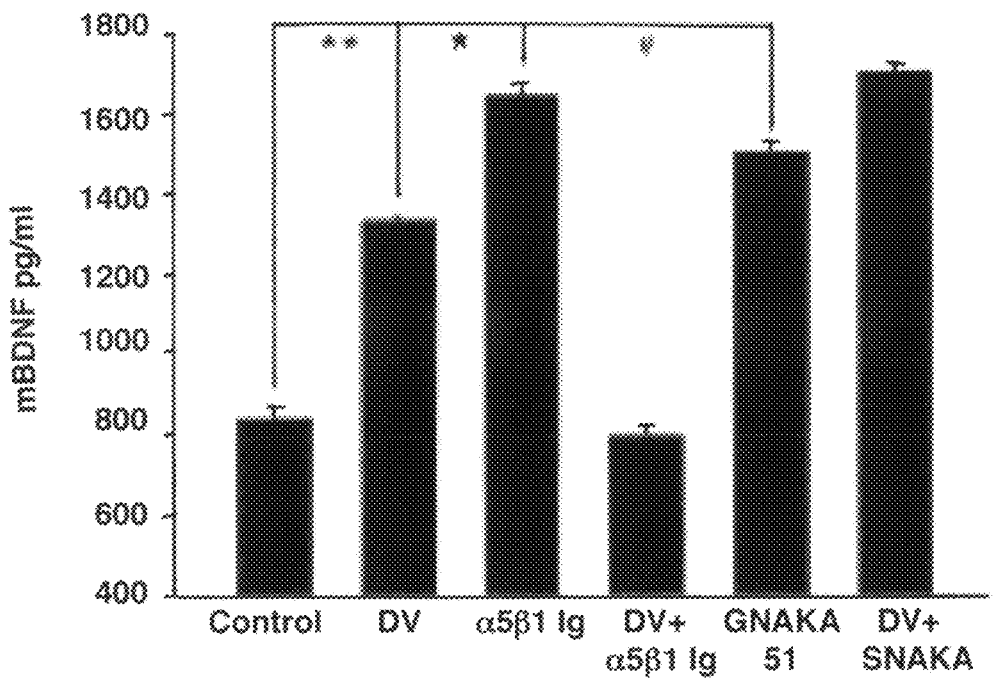
FIGS. 12A-12B show the effects of Domain V on BDNF.
Figure 12B:
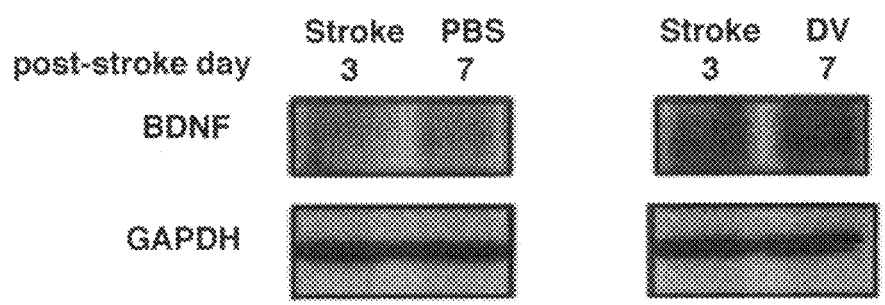
Figure 12C:
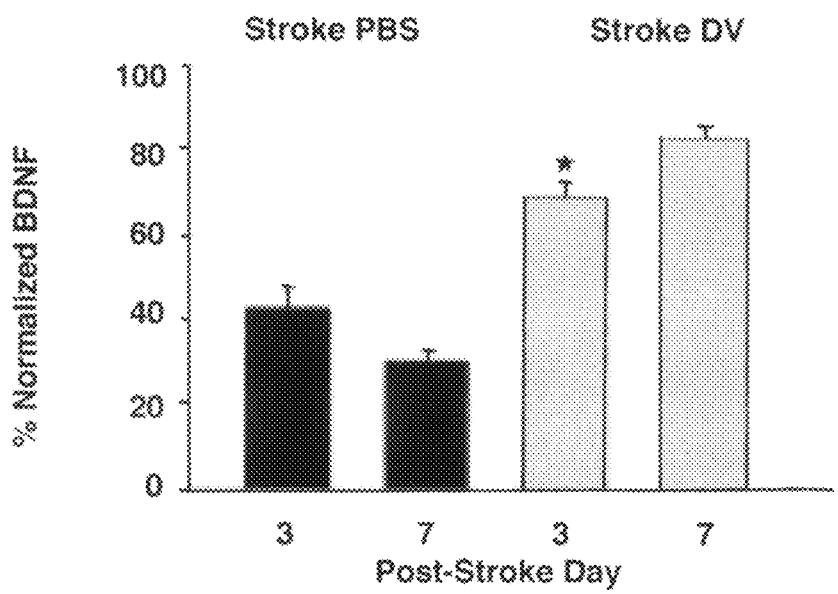
FIG. 12C: Quantification of BDNF western blots demonstrating a significant increase in post-stroke BDNF levels on post-stroke days 3 and 7 (*p=0.006, **p=0.0001) with Domain V treatment as compared to the corresponding day in PBS treated animals, mean values+/−standard error from 3 separate western blots shown.

In vivo results herein suggest that DV treatment favored neurovascular brain repair which could be due in part to DV-induced release of neurovascular promoting factors such as brain-derived neurotrophic factor (BDNF). FIG. 12A demonstrates that after 24 hours, DV significantly (** p=0.0025) enhances brain microvascular endothelial cell BDNF release. Similarly, post-stroke DV treatment resulted in a significant increase in stroked brain BDNF levels (FIGS. 12B-12C) on post-stroke days 3 and 7, as compared to PBS treated controls. Furthermore, no effect on BDNF levels was seen with DV addition to primary isolated rat astrocytes or cortical neurons suggesting that DV effects on in vivo brain BDNF levels may be primarily brain endothelial cell mediated.

EXAMPLE 25

Domain V Interacts with and Exerts its Pro-Angiogenic Effects Via the α5β1 Integrin As brain microvascular endothelial cells do not express the previously identified DV receptor α2β1 integrin, DV's pro-angiogenic effect on brain endothelial cells might be due to both the absence of α2β1 and the presence of a distinct pro-angiogenic DV receptor. α5β1 is critical for vascular development and promotes post-stroke brain angiogenesis, but is otherwise downregulated in mature brain until re-expressed in brain endothelial cells after hypoxia. A monomeric variant of the angiogenesis promoting growth factor angiopoetin 1 binds to and promotes vascular stabilization via the α5β1 integrin, further underscoring this receptor's importance in angiogenesis and vascular remodeling.

It was first determined whether specific activation of the α5β1 integrin could affect BDNF levels. FIG. 12A demonstrates that cell treatment with an α5β1 antibody that specifically recognizes the α5 ligand binding domain, was by itself capable of increasing BDNF release. Furthermore, SNAKA51, an antibody that activates the α5β1 integrin by binding to a region outside of the ligand binding domain and thereby priming α5β1 to bind ligand, significantly increased BDNF levels (p=0.0007). Interestingly, the simultaneous addition of α5β1 antibody and DV inhibited BDNF release while simultaneous addition of DV and SNAKA51 further increased BDNF levels (p=0.06). This is consistent with the hypothesis that DV increases BDNF release by binding the α5 ligand binding domain.

Figure 13A:
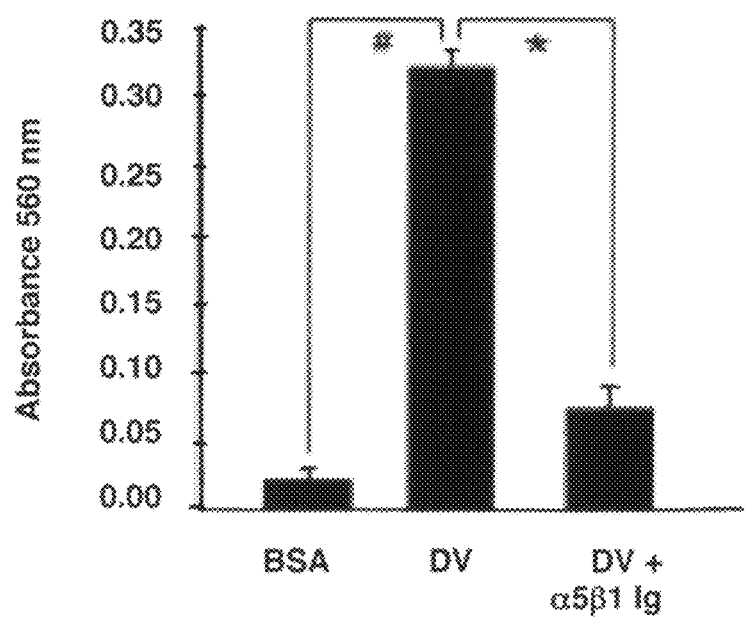
Figures 13B, 13C:
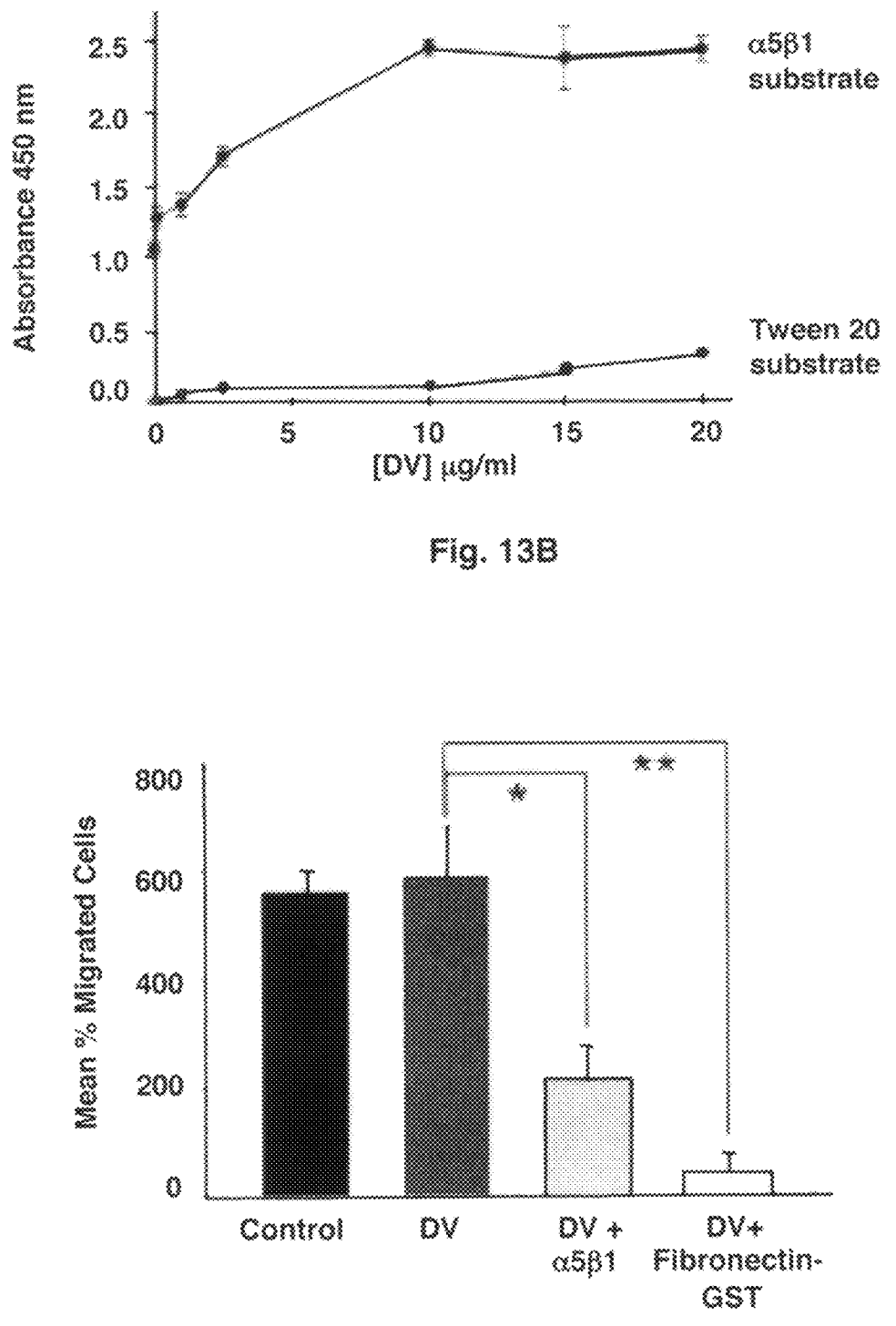
Figure 13D:
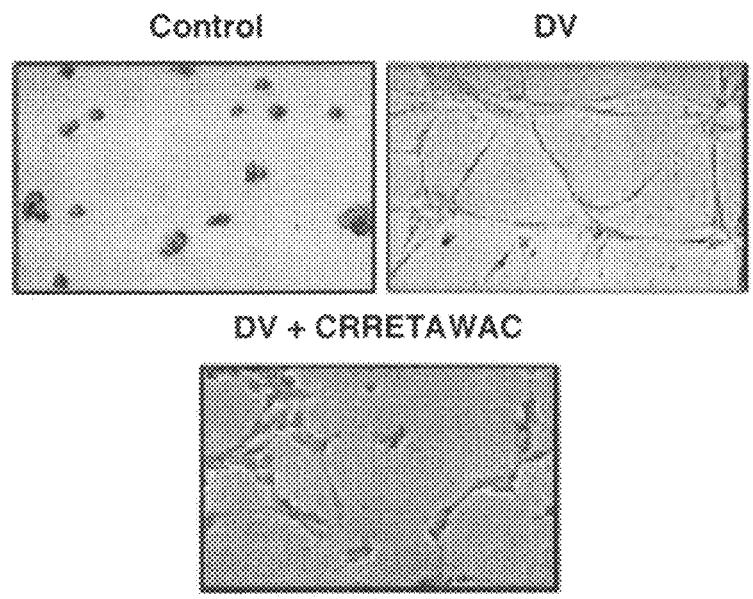
Figure 13E:
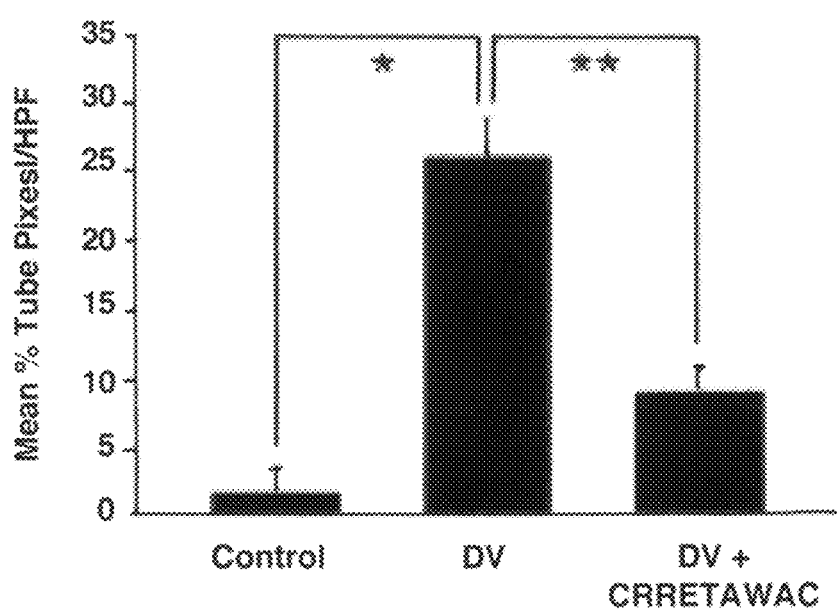

Whether brain microvascular endothelial cell adhesion to DV could depend on α5β1 was examined by demonstrating that α5β1 antibody directed against the α5 ligand binding domain could prevent their adhesion to immobilized DV (FIG. 12A). By ELISA with recombinant α5β1 integrin, it was demonstrated that DV binds to α5β1 in a dose dependent fashion with a $K_d$ of approximately 30 nM (FIG. 13B). To further link DV's pro-angiogenic effects with α5β1, it was demonstrated that brain endothelial cell migration towards DV could be inhibited by both fibronectin-GST and soluble α5β1-GST (FIG. 13C). Furthermore, the α5β1 specific binding peptide CRRETAWAC (SEQ ID NO: 3) could significantly (p=0.001) inhibit DV's effects on brain endothelial cell tube formation in vitro (FIGS. 13D-13E).

Figure 13F:
Figure 13G:
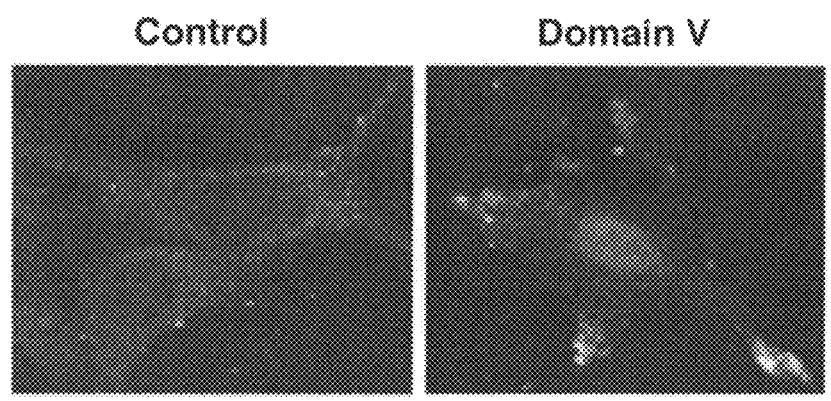
Figure 13H:
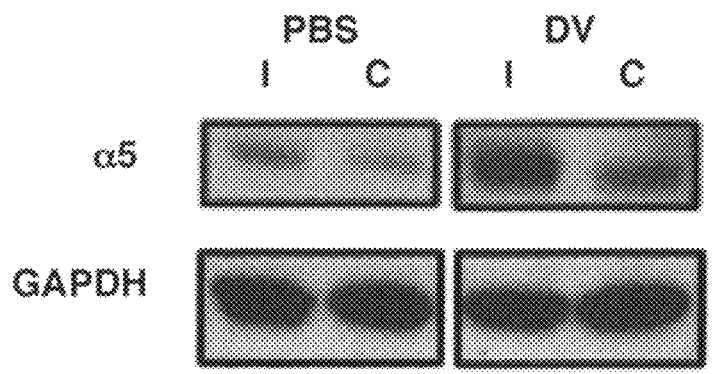

To address whether DV increases brain angiogenesis in part by increasing brain endothelial cell expression of α5β1, DV treatment of confluent brain endothelial cell monolayers over 8 hours maintained total α5β1 protein levels that otherwise significantly diminished in serum-free control conditions (FIG. 13F). Furthermore, DV treatment of brain endothelial cells grown on plastic significantly redistributed α5β1 integrin to surface/lamellipodia (FIG. 13G), but had no effect on α5β1 surface expression in astrocytes or primary cortical neurons. Lastly, to determine whether DV might also affect α5β1 integrin levels in vivo, western blot analysis of brain lysate from the stroked and contralateral hemispheres of post-stroke day 3 animals+/−DV treatment were performed (FIG. 13H) and observed significantly more α5β1 integrin in stroke brain tissue treated of DV treated animals (p=0.00004, quantification not shown). Collectively, these results suggest that DV binds to, affects the expression of, and exerts its pro-angiogenic effect via the α5β1 integrin.

α2β1 Integrin Reverses DV Cell Proliferation Activity

Figure 14A:
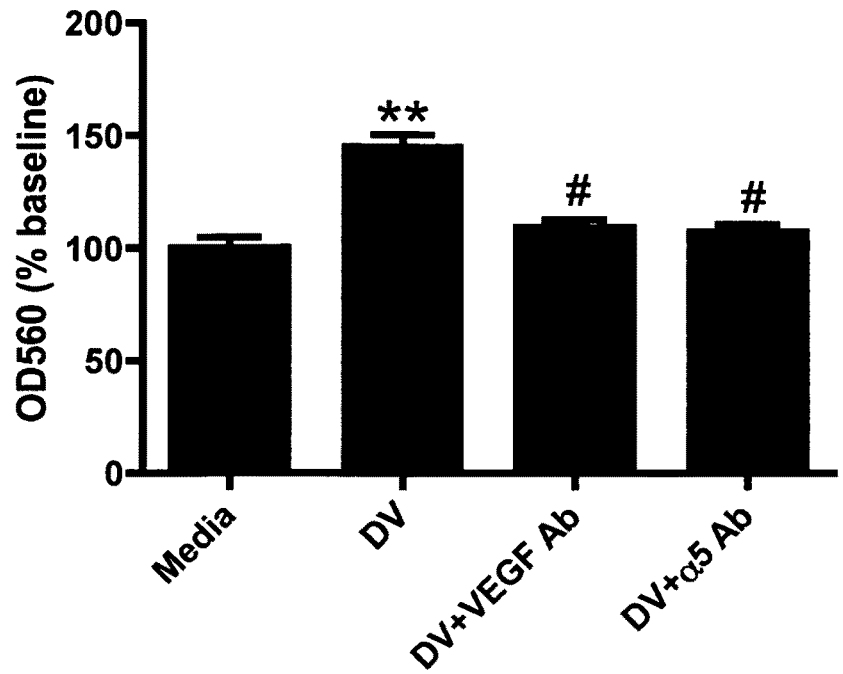
FIGS. 14A-14B show the effects of α2β1 on DV cell proliferative activity in C57 cells.
Figure 14B:
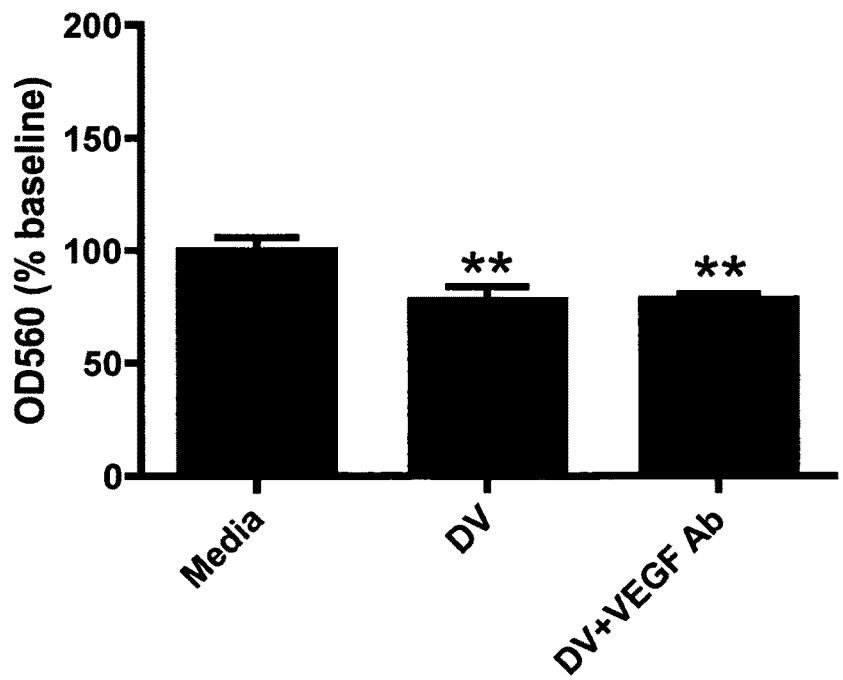

Addition of α2β1 integrin to C57 mouse brain endothelial cells reverses Domain V cell proliferative activity. As DV is anti-angiogenic in most endothelial cells that express both α2β1 integrin (anti-angiogenic receptor) and α5β1 integrin (pro-angiogenic receptor), it was contemplated that DV is anti-angiogenic in these cells due to its increased affinity for α2β1 integrin (Kd around 30 nM) over α5β1 integrin (Kd 160 nM). α2β1 integrin was transfected into mouse brain microvascular endothelial cells that do not normally express this receptor. This was accomplished by transfection with a plasmid vector (pEGFP-N2, Clontech) containing a sequence encoding the α2-subunit integrin with a C-terminal RFP fusion protein (Texas A&M University Biomedical Engineering), empty vector was used as a control. Cells were allowed to recover during 24 h in medium containing no antibiotics. Transfection efficiency was appreciated after 24 h using an inverted fluorescent microscope. Cell proliferation was assessed after 48 hours in serum free media with MTS solution (Promega, Madison, Wis.) following the manufacturer's instructions. DV increases the proliferation of mouse brain endothelial cells, as compared to cell media control, which can be blocked by the addition of VEGF neutralizing antibody or α5β1 integrin function blocking antibody (FIG. 14A). The addition of α2β1 integrin to the cells suppresses rather than increases the growth of the cells demonstrating that the addition of α2β1 integrin to mouse brain endothelial cells converts DV from being proliferative to anti-proliferative. Bars are mean values+/−standard deviation (FIG. 14B). **p<0.01. ##p<0.01.

Kinetics of Binding of DV to A5

Binding assays were carried out using an optical biosensor (IAsys; Affinity Sensors, UK) as described (17). In brief, to covalently bind the A5 domain, designated as an acceptor, onto the surfaces of a sensor, carboxylate groups present on the surface were activated by injection of a 1:1 mixture of 0.1 M N-hydroxysuccinimide and 0.4 M N-Ethyl-3-(3-dimethylaminopropyl) carbodiimide (Pierce). The acceptor dissolved in phosphate buffered saline (PBS) was then allowed to bind to the activated surface until a response plateau was reached. The residual active groups were blocked by an injection of 100 μL of 1 M Tris-HCl (pH 8.5).

A cuvette with immobilized A5 was primed with the binding buffer (150 mM NaCl, 25 mM Tris-HCl, pH=7.4, and 1 mM $MnCl_2$) at 25° C. for 10 min. A 100-μL sample containing free DV interactant dissolved in the binding buffer was added to the cuvette, and then the association phase was recorded. Subsequently, the sample was removed, analyte-free buffer was added to the cuvette, and the dissociation phase was recorded. After each assay, the surface of the cuvette was regenerated by a brief wash with 100 mM glycine, pH=4, followed by equilibration with the binding buffer. During regeneration cycles attention was paid to complete removal of the surface-bound analyte, and the washing continued until a response equal to a baseline value was reached.

For binding assays, free DV was added at concentrations ranging from $8.0 \times 10^{-8}$ M to $4.0 \times 10^{-7}$ M. Data from the biosensor were analyzed by the global fitting method, as described (18). For each assay, the association rate constants ($k_{on}$) and the dissociation rate constants ($k_{off}$) were obtained, and the equilibrium dissociation constants ($K_d$) values were calculated from a ratio of $k_{off}/k_{on}$. In addition, control binding of bovine serum albumin (BSA) at the molar concentration of $8.0 \times 10^{-7}$ (double of the highest concentration for DV was also performed. As shown in Table 1, DV binds to the α5β1 integrin.

TABLE 1

| $k_{on}$ [M$^{-1}$s$^{-1}$] | $k_{off}$ [s$^{-1}$] | $K_d$ ($K_d = k_{off}/k_{on}$) [M] |
|---|---|---|
| $3.8 \times 10^6 \pm 2.7 \times 10^5$ | $7.2 \times 10^{-1} \pm 1.1 \times 10^{-1}$ | $1.6 \times 10^{-7} \pm 7.2 \times 10^{-8}$ |

These studies demonstrate that the extracellular matrix-derived inhibitor of angiogenesis, perlecan DV, is stably and chronically generated in stroke injured brain. Quite unexpectedly, administered DV enhances rather than inhibits brain angiogenesis in vitro and in vivo. DV homes to stroke and peri-infarct brain tissue, enhances neurovascular niche formation, due at least in part to enhanced BDNF release, and ultimately improves functional motor outcome to baseline pre-stroke levels in endothelin-1 and tandem ipsilateral CCA & MCA stroke models in rats and mice, respectively. Finally, DV enhances brain endothelial cell angiogenesis, in the absence of the α2β1 integrin, via the α5β1 integrin.

Perlecan, synthesized and secreted by neurons, astrocytes, and endothelial cells, induced in the latter by $VEGF_{165}$, has the distinction of being the most sensitive and rapidly processed matrix component after stroke. Perlecan proteolysis by cathepsin L occurs within 2 h of the occlusion of the middle cerebral artery in nonhuman primates and persists for several days. The sustained processing of perlecan for days after stroke is consistent with studies demonstrating an increase in perlecan production in neurons and astrocytes after brain injury. In the present study, there was a rapid increase in perlecan DV levels that gradually plateaus at an elevated level over the course of seven days, a temporal pattern that correlates well with the nonhuman primate post-stroke perlecan proteolysis profile.

The ability of an anti-angiogenic extracellular matrix fragment to promote brain angiogenesis may be due to the concept of endothelial heterogeneity, whereby endothelial cells in different, vascular beds, in this case brain versus nonbrain, respond differently to angiomodulatory factors. This differential response may be due to differences in respective microenvironments, differences in expressed receptors, such as the presence or absence of α2β1 integrin, or differences in signal transduction components. Additionally, the type XVIII collagen-derived inhibitor of angiogenesis, Endostatin, promotes angiogenesis in immature endothelial cells derived from differentiated embryonic stem cells raising the possibility that angiogenic brain endothelia function or behave like immature endothelia. Indeed, newly angiogenic brain endothelia undergo an integrin receptor switch after brain hypoxia from mature integrin receptors back to developmental integrin expression, particularly, the α5β1 integrin.

The enhanced post-stroke expression of α5β1 integrin might also explain DV's ability to home to the stroke and peri-infarct cortex vasculature just as tumor vasculature expressing α2β1 supported DV targeting in vivo. Additionally, the near immediate post-stroke proteolysis of perlecan and generation of DV could serve as part of the trigger of the integrin receptor switch. This is supported by the observation that DV increased total expression of α5β1 integrin on brain endothelial cells in vitro and α5β1 integrin levels in post-stroke brain tissue.

The present invention also shows that DV stimulates BDNF release. BDNF is both pro-angiogenic, neuroprotective, and stimulates neuronal migration and neural stem cell renewal. BDNF is critical to rehabilitation-induced recovery after stroke in rats.

Focal cerebral ischemia causes the disruption of the blood-brain barrier that is manifested as a loss in microvascular integrity and leakage of plasma constituents into the extravascular space. Furthermore, prevention of early increases in permeability may be beneficial for injury outcome. nDV may perform this function and perhaps even improve barrier function within this time frame thus reducing the degree of injury. Intriguingly, the same proteolytic process that breaks down the vascular extracellular matrix and directly contributes to acute stroke vascular leakage also generates DV, suggesting that stroke-induced vascular matrix proteolysis is not completely deleterious. Subsequent DV-induced permeability after 8 h may indicate a role in early vascular remodeling that contributes to a rapid re-establishment of a steady state for oxygen delivery. Notably, the DV-induced increase in microvascular permeability precedes the 24-48 h second phase of barrier leakage seen in stroke models further lending weight to this possibility.

EXAMPLE 26

DV does not Significantly Affect Blood Brain Barrier Permeability In Vivo

Because it was demonstrated that DV could decrease TEER in brain endothelial cells in vitro, a potentially worrying effect post-stroke where blood brain barrier permeability is already negatively impacted, it was determined whether DV had any effect on blood brain barrier permeability in vivo.
Material and Methods

[$^3$H]mannitol (14.2 Ci/mmol) and [$^{14}$C]sucrose (412 mCi/mmol) were purchased from Moravek Biochemicals (USA). The remaining chemicals were purchased from Sigma Chemical Company (UK). Mice were purchased from Harlan, UK.

All experiments were performed within the guidelines of the Animals Scientific Procedures Act (1986, UK). Adult male BALB/c (27.3±0.3 g) and C57Bl6 (27.9±0.6 g) mice were anaesthetised (i.p. medetomidine hydrochloride (2 mg/kg) and ketamine (150 mg/kg)) and heparinised (100 U, i.p.) and the in situ brain perfusion technique performed by cannulation of the left ventricle of the heart and sectioning of the right atria as described by Sanderson et al., 2007. The artificial plasma contained [$^3$H]mannitol (35.2 nM; 182 Da; radius=3.6 Å) and [$^{14}$C]sucrose (1.1 mM; 342 Da; radius 4.6 Å) and perfusion was for 10 minutes. After which the animal was decapitated and brain regions (frontal cortex, occipital cortex, caudate nucleus, hippocampus, hypothalamus, thalamus, cerebellum, pons) taken for liquid scintillation counting. The amount of tissue radioactivity was expressed as a percentage of that in the artificial plasma and termed $R_{Tissue}\%$ (ml. 100 g$^{-1}$). Separate groups of mice were given DV (1 mg/kg) dissolved in PBS vehicle and the in situ brain perfusion procedure performed at 2, 8 and 24 hours post-injection. These experimental groups were compared to animals which has received vehicle only. The effect of DV on brain (anterior central gyrus) water content was also examined at the time points studied. Two Way ANOVA or One Way ANOVA was applied to the data using GraphPad Prism 5.0 software package (GraphPad Software Inc.).

Effects of DV on Vascular Space in Mice

Figure 15A:
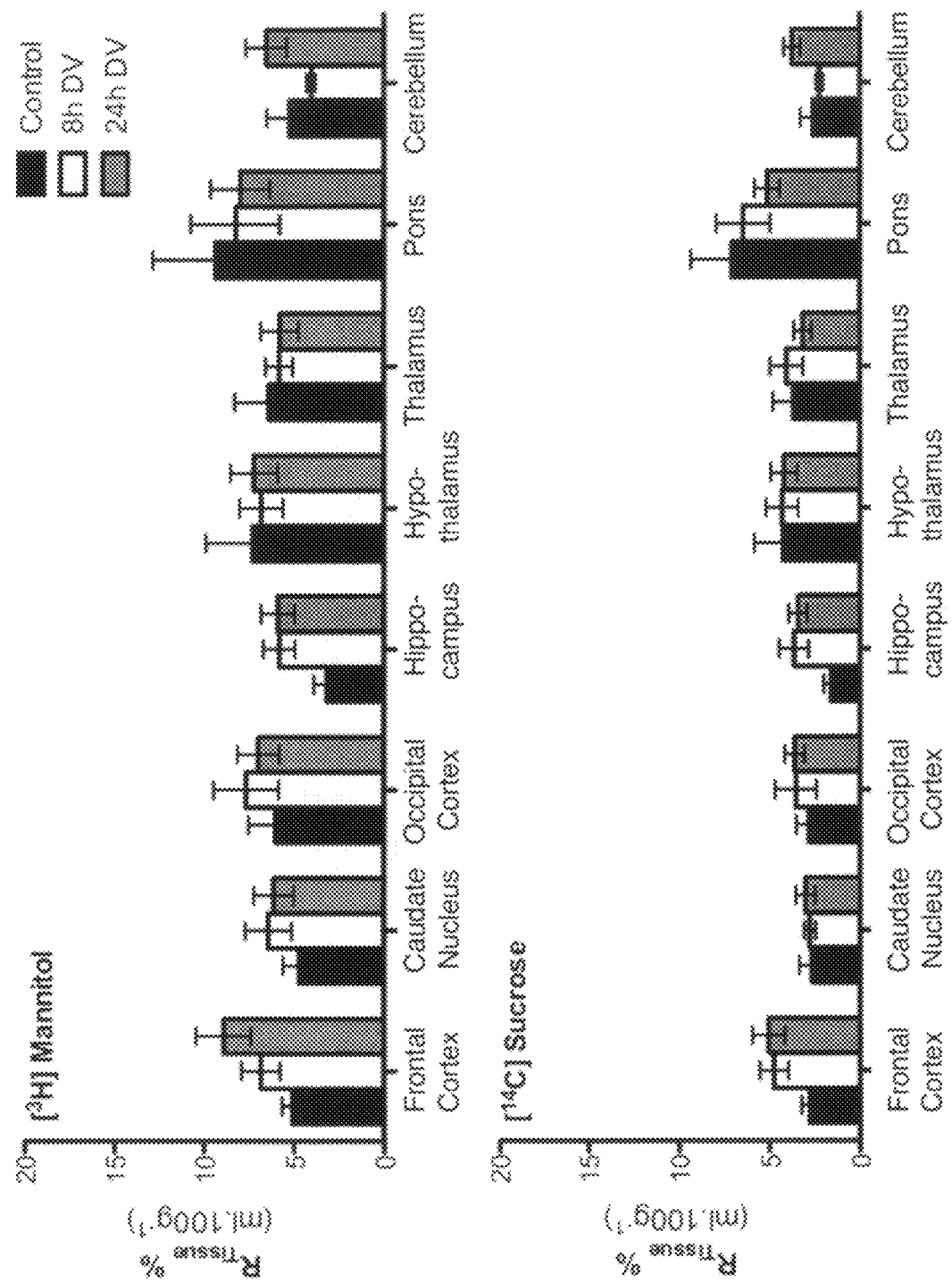
FIGS. 15A-15B show the effects of DV on the intervascular space in Balb/c (FIG. 15A) and C57BI6 (FIG. 15B) strains of mice.
Figure 15B:
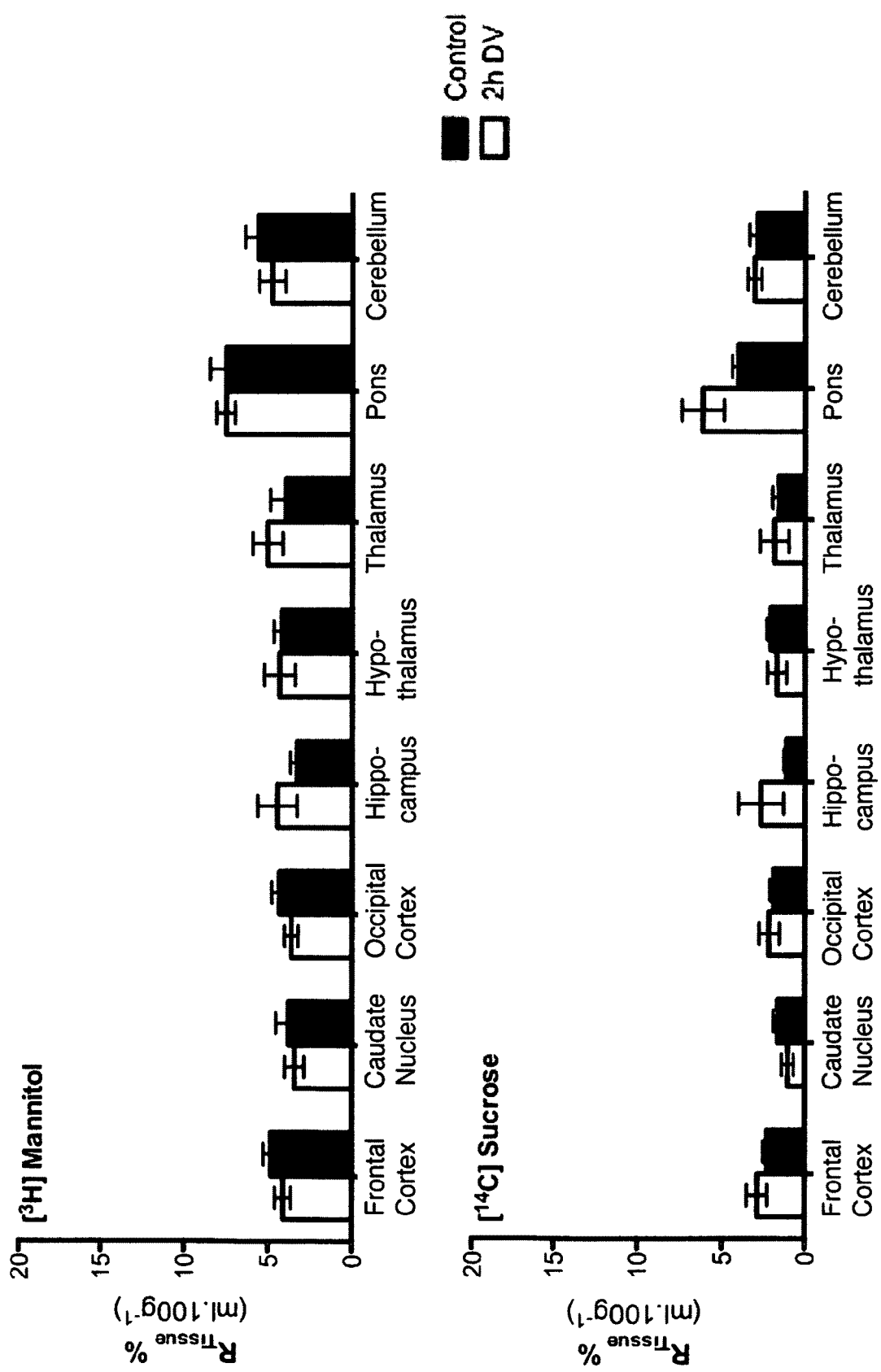

In the BALB/c strain the vascular space in all brain regions as measured by [$^{14}$C]sucrose and [$^{3}$H]mannitol was not significantly affected 8 or 24 hours after an intraperitoneal injection of DV (1 mg/kg, FIG. 15A). Furthermore the brain water content was 73.3±1.3% at 0 hours and was not significantly affected 8 (64.6±3.4%) or 24 (72.8±2.9%) hours by the intraperitoneal injection of DV (1 mg/kg) (One Way ANOVA). In the C57Bl6 strain the vascular space in all brain regions, as measured by [$^{14}$C]sucrose and [$^{3}$H]mannitol, was not significantly affected 2 hours after an intraperitoneal injection of DV (1 mg/kg, FIG. 15B).

The following references are cited herein.
1. Ohab et al. J Neurosci, 26:13007-16 (Dec. 13, 2006).
2. Mundel et al. Microvascular Research, 74:85-9 (2007).
3. Bix et al., Trends Cell Biol, 15:52-60 (2005).
4. Bix et al. J Natl Cancer Inst, 98:1634-46 (2006).
5. Bix et al. J Cell Biol, 166:97-109 (2004).
6. Schallert et al. Adv. Neurol. 73:229-238 (1997).
7. O'Reilly et al., Cell, 88:277 (1997).
8. Sapatino et al. In Vitro Cell Dev Biol, 29A:923-8 (1993).
9. Bix et al. Blood, 109:3745-8 (2007).
10. Asou et al. Neuroscience Letters, 144:221-4 (1992).
11. Fukuda et al. Stroke, 35:1364-70 (Apr. 1, 2004).
12. Auerbach et al. Clin Chem, 49:32-40 (Jan. 1, 2003).
13. Bix et al. J Neurosci, 18:307-18 (Jan. 1, 1998).
14. Hirotsune et al. Nature Genetics, 19:333 (August 1998).
15. Milner et al. Stroke, 39:191-7 (Jan. 1, 2008).
16. Aronowski et al. Journal of Cerebral Blood Flow & Metabolism, 19:652-60 (Jun. 19, 1999).
17. Brittingham, et al. J Biol Chem 280:191-198 (2005).
18. Myszka and Morton. Trends Biochem Sci, 23:149-150 (1998).

What is claimed is:

1. A method of stimulating or enhancing angiogenesis in the brain of a stroke patient comprising administering to a patient having had a stroke a therapeutically effective amount of an endorepellin protein having the amino acid sec uence of domain V of erlecan and stimulating or enhancing angiogenesis in the brain of said stroke patient.

2. The method of claim 1, wherein said endorepellin protein having the amino acid sequence of domain V of perlecan is administered orally.

3. The method of claim 1, wherein said endorepellin protein having the amino acid sequence of domain V of perlecan is administered in an amount from about 0.1 mg/kg to about 10 mg/kg of the patient's body weight.

4. The method of claim 1, wherein said administration of a therapeutically effective amount of an endorepellin protein having the amino acid sequence of domain V of perlecan results in brain endothelial cell capillary tube formation within neurons.

5. The method of claim 1, wherein said administration of a therapeutically effective amount of an endorepellin protein having the amino acid sequence of domain V of perlecan results in increased expression of the pro-angiogenic $\alpha 5\beta 1$ integrin in brain endothelial cells.

6. The method of claim 1, wherein said patient has had an ischemic stroke.

7. The method of claim 1, wherein said administration of a therapeutically effective amount of an endorepellin protein having the amino acid sequence of domain V of perlecan results in improved functional stroke outcome for said patient.

\* \* \* \* \*

UNITED STATES PATENT AND TRADEMARK OFFICE
CERTIFICATE OF CORRECTION

PATENT NO. : 8,466,105 B2
APPLICATION NO. : 12/655503
DATED : June 18, 2013
INVENTOR(S) : Gregory J. Bix Page 1 of 1

It is certified that error appears in the above-identified patent and that said Letters Patent is hereby corrected as shown below:

In the Specification

Column 3,
Lines 2-3, "and payment of the necessary fee.
FIGS 1A-1B show"
should read
--and payment of the necessary fee.
The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.
FIGS 1A-1B show--.

Column 9,
Line 33, "endothelialn" should read --endothelial--.

Column 12,
Line 11, "above±endothelial" should read --above ± endothelial--.

Column 16,
Line 58, "chamber±preincubation" should read --chamber ± preincubation--.

Column 22,
Line 61, "acid sec uence" should read --acid sequence--.
Line 62, "of erlecan" should read --of perlecan--.

Signed and Sealed this
First Day of October, 2013

Teresa Stanek Rea
*Deputy Director of the United States Patent and Trademark Office*